(12) United States Patent
Marx et al.

(10) Patent No.: US 7,566,531 B2
(45) Date of Patent: Jul. 28, 2009

(54) SELECTIVE WHOLE CELL QUARTZ CRYSTAL MICROBALANCE BIOSENSORS

(75) Inventors: Kenneth A. Marx, Francestown, NH (US); Susan J. Braunhut, Wellesley, MA (US); Tiean Zhou, Lowell, MA (US); Anne Rugh, Dover Plains, NY (US)

(73) Assignee: University of Massachusetts, Boston, MA (US)

( * ) Notice: Subject to any disclaimer, the term of this patent is extended or adjusted under 35 U.S.C. 154(b) by 853 days.

(21) Appl. No.: 10/793,386

(22) Filed: Mar. 3, 2004

(65) Prior Publication Data

US 2004/0235198 A1 Nov. 25, 2004

Related U.S. Application Data

(60) Provisional application No. 60/451,583, filed on Mar. 3, 2003.

(51) Int. Cl.
  *G01N 33/551* (2006.01)
  *G01N 33/552* (2006.01)
  *G01N 33/554* (2006.01)
  *G01N 33/569* (2006.01)
  *G01N 33/574* (2006.01)

(52) U.S. Cl. .......... 435/5; 422/82.01; 435/7.1; 435/7.2; 435/7.23; 435/7.31; 435/7.32; 435/287.2; 436/524; 436/527; 436/64; 436/149; 436/806; 310/311; 310/313 R; 310/340

(58) Field of Classification Search ............. None
See application file for complete search history.

(56) References Cited

U.S. PATENT DOCUMENTS

| 4,789,804 A | * | 12/1988 | Karube et al. | 310/311 |
| 4,999,284 A | * | 3/1991 | Ward et al. | 435/4 |
| 5,658,732 A | * | 8/1997 | Ebersole et al. | 435/6 |
| 5,705,399 A | * | 1/1998 | Larue | 436/501 |
| 5,814,525 A | * | 9/1998 | Renschler et al. | 436/524 |
| 6,033,852 A | * | 3/2000 | Andle et al. | 435/6 |

OTHER PUBLICATIONS

"QMC—Construction of a biosensor using QCM-D". Lab-PM laboration III in Biomaterials and Biophysics on Surfaces (4p). Skapad av Karin Glasmästar och Erik Reimhuit, 2000. Updated 2001.

Hsien-Chang Chang et al. "Detection of lipopolysaccharide binding peptides by the use of a lipopolysaccharide-coated piezoelectric crystal biosensor". Analytica Chimica Acta 340:49-54, 1997.

C. Fredriksson et al. "The Piezoelectric Quartz Crystal Mass and Dissipation Sensor: A Means of Studying Cell Adhesion". Langmuir 14:248-251, 1998.

David M. Gryte et al. "Real-time Measurement of Anchorage-Dependent Cell Adhesion Using a Quartz Crystal Microbalance". Biotechnol. Prog. 9:105-108, 1993.

(Continued)

*Primary Examiner*—Christopher L Chin
(74) *Attorney, Agent, or Firm*—Fish & Richardson P.C.

(57) ABSTRACT

Selective whole cell QCM biosensors are disclosed. Also disclosed are methods of making and using such whole cell QCM biosensors, e.g., to screen drugs and diagnose diseases.

55 Claims, 14 Drawing Sheets

OTHER PUBLICATIONS

Kenneth A. Marx et al. "Quartz Crystal Microbalance Measurement of Self-Assembled Micellar Tubules of the Amphiphilic Decyl Ester of D-Tyrosine and Their Enzymatic Polymerization". Biotechnol. Prog 15:522-528, 1999.

Kenneth A. Marx et al. "A quartz crystal microbalance cell biosensor: detection of microtubule alterations in living cells at nM nocodazole concentrations". Biosensors & Bioelectronics 16:773-782, 2001.

Hiroshi Muramatsu et al., "Reliability of correlation between mass change and resonant frequency change for a viscoelastic-film-coated quartz crystal". Journal of Electroanalytical Chemistry 388:89-92, 1995.

Ghada Nimeri et al. "Neutrophil interaction with protein-coated surfaces studied by an extended quartz crystal microbalance technique". Colloids and Surfaces B: Biointerfaces 11:255-264, 1998.

Karl D. Pavey. "Quartz crystal analytical sensors: the future of label-free, real-time diagnostics". Expert Rev. Mol. Diagn. 2(2):173-186, 2002.

Robert J. Vasquez et al. "Nanomolar Concentrations of Nocodazole Alter Microtubule Dynamic Instability In Vivo and In Vitro". Molecular Biology of the Cell 8:973-985, Jun. 1997.

Joachim Wegener et al. "Cell adhesion monitoring using a quartz crystal microbalance: comparative analysis of different mammalian cell lines". European Biophysics Journal 28(1):26-37, 1998.

Joachim Wegener et al. "Analysis of the Composite Response of Shear Wave Resonators to the Attachment of Mammalian Cells". Biophysical Journal 78:2821-2833, Jun. 2000.

Tiean Zhou et al. "Cellular Adhesion and Spreading of Endothelial Cells Monitored in Real-time Using the Quartz Crystal Microbalance". Mat. Res. Soc. Pymp. Proc. 550:177-182, 1999.

Tiean Zhou et al. "The Quartz Crystal Microbalance as a Continuous Monitoring Tool for the Study of Endothelial Cell Surface Attachment and Growth". Biotechnol. Prog. 16:258-277, 2000.

* cited by examiner

SEQUENCE LISTING

```
<160> NUMBER OF SEQ ID NOS: 4

<210> SEQ ID NO 1
<211> LENGTH: 3
<212> TYPE: PRT
<213> ORGANISM: Artificial Sequence
<220> FEATURE:
<223> OTHER INFORMATION: Synthetically generated peptide

<400> SEQUENCE: 1

Arg Gly Asp
 1

<210> SEQ ID NO 2
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 2

Tyr Ile Gly Ser Arg
 1               5

<210> SEQ ID NO 3
<211> LENGTH: 4
<212> TYPE: PRT
<213> ORGANISM: Artificial Sequence
```

-continued

```
<220> FEATURE:
<223> OTHER INFORMATION: Synthetically generated peptide

<400> SEQUENCE: 3

Arg Gly Asp Tyr
 1

<210> SEQ ID NO 4
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 4

Arg Asp Gly Tyr
 1
```

SELECTIVE WHOLE CELL QUARTZ CRYSTAL MICROBALANCE BIOSENSORS

CROSS-REFERENCE TO RELATED APPLICATION

This application claims the benefit of priority from U.S. Provisional Application Ser. No. 60/451,583, filed on Mar. 3, 2003, the contents of which is incorporated herein by reference in its entirety.

TECHNICAL FIELD

This invention relates to whole cell quartz crystal microbalance biosensors for diagnosis and drug discovery.

BACKGROUND

The Quartz Crystal Microbalance (QCM) was developed and initially used to measure chemical species in a gas phase. Solution-based QCM has been a more recent development, and is largely used, e.g., as a tool in analytical electrochemistry. Using the Sauerbray equation (Sauerbray et al., Z. Physiol., 155:206-222, 1959), the QCM is capable of sensitively measuring mass changes associated with liquid-solid interfacial phenomena, particularly at electrodes. Surface bound elastic mass can be distinguished from viscoelastic behavior of bound mass or solution viscosity-density effects on the crystal frequency (f), and resistance (R), using established techniques.

Biosensors have been created using the QCM piezoelectric signal transduction mechanism, in which a range of biological macromolecules has been incorporated into the sensing system design. In some of these biosensors, whole cells have been studied on the QCM surface. Surface adherent cell types previously studied include: endothelial cells, osteoblasts, human platelets, MDCK I and II cells, 3T3 cells, CERO cells, CHO and MKE epithelial cells, and microbial biofilms (see, e.g., Marx et al., Biosens. Bioelectron., 16(9-12):773-82, 2001). These studies establish the basic principle that adherent cells produce a reversible QCM frequency (f) shift and resistance (R) shift. The cells adhere to the QCM surface to reach a steady state condition defined by stable QCM $\Delta f$ and $\Delta R$ shift values in a cell-number dependent manner. Once this steady state condition has been reached, the cells within the QCM can be used as a biosensor, i.e., a whole cell QCM biosensor. However, it takes a relatively long time for the cells to reach a steady state on the QCM surface.

SUMMARY

The present invention relates to a whole cell biosensor that ensures rapid and highly accurate quantification of a specific component contained in a sample. The invention is based, in part, on the discovery that a precise and selective biosensor can be prepared by applying to a surface of a QCM a selective substrate film that allows specific cells to attach and spread over the surface and quickly achieve a steady state. Once the cells are attached, the new whole cell QCM biosensor can be used soon after cell addition so that reproducible, sensitive, and accurate test results can be rapidly obtained.

In one aspect, the invention features a biosensor. The biosensor contains a quartz crystal microbalance and a selective substrate film disposed onto a surface of a conducting element of the quartz crystal microbalance. The selective substrate contains one or more binding sites that are covalently bound to the selective substrate film. A "selective substrate" or "selective substrate film," as used herein, is any material that can be modified to contain binding sites appropriate for the attachment or association of cells, and that can be deposited or applied to a surface of a QCM. Possible selective substrate materials include, but are not limited to, synthetic polymers (e.g., pyrroles or thiophenes, anilines, and their derivatives), biological polymers (e.g., peptides, nucleotides, and carbohydrates), and composites formed from these materials. A "binding site" or "binding moiety" in or on the selective substrate on a QCM is a compound or molecule, e.g., a peptide, that directs specific binding of a cell, e.g., an epithelial cell, to the surface of the QCM. In one embodiment, a cell is attached to the selective substrate.

In another aspect, the invention features methods for screening test agents for their ability to affect a cell. The method includes placing one or more cells onto a biosensor as described herein, contacting the agent to the cell(s), monitoring a parameter of the quartz crystal microbalance, and comparing the parameter with a predetermined value. A difference between the parameter and the predetermined value indicates that the agent has affected the cell.

A "test agent" or "test compound," or grammatical equivalents, is any molecule, e.g., protein, polypeptide, oligopeptide, small organic or inorganic molecule, polysaccharide, or polynucleotide, to be tested for the ability to directly or indirectly alter a cellular phenotype, including cell attachment. In some embodiments, a plurality of assay mixtures can be run in parallel with different test compounds. A test compound (agent) that has been tested to have a desired ability is referred as "candidate compound (agent)." A "polypeptide" is any chain of amino acids, regardless of length or post-translational modification (e.g., glycosylation or phosphorylation).

By "contacting," "administering," or "applying" is meant that a test or candidate compound is added to the cells in such a manner as to allow the compound to act upon the cells, whether by uptake and intracellular action, or by action at the cell surface. In some embodiments, a nucleic acid encoding a peptide may be added to the cells, such that the peptide is expressed in the cell.

In another aspect, the invention features methods of evaluating the metastatic potential of a test cell from a subject. The methods include placing a test cell onto a first biosensor described herein, placing a control cell onto a second biosensor described herein, monitoring a parameter of the QCM in the first biosensor and the same parameter of the QCM in the second biosensor, and comparing the parameters. A difference between the parameters indicates the metastatic potential of the test cell.

In yet another aspect, the invention features methods of making a biosensor. The methods include obtaining a quartz crystal microbalance and synthesizing a selective substrate film onto the surface of conducting element of the quartz crystal microbalance. In certain embodiments, the methods further include placing one or more cells onto the selective substrate film.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF DRAWINGS

FIG. 1A shows signal transduction elements. FIG. 1B shows an entire whole cell QCM biosensor measurement system. FIGS. 1C and 1D show whole cell QCM biosensor measurement systems including different data analyzing units.

FIG. 4A: Single exponential fits: $\Delta f = 13.50 \; e0.02722N (R^2=0.9770)$, and $\Delta R = 2.104 \; e0.0360N \; (R^2=0.9960)$; Insert: double logarithmic plots of $\Delta f$ and $\Delta R$ as functions of cell numbers. FIG. 4B: Open circles: 1 hour data and best fit with a three-component sigmoid curve; Filled circles: 24 hour data and best fit with a hyperbolic curve.

DETAILED DESCRIPTION

There is a need for more sensitive biosensors and sensing methods to analyze chemical and biological materials. A new whole cell biosensor, with a more uniform surface, tailored to facilitating cell attachment of specific cells, is described herein. Such a selective whole cell QCM biosensor, allows specific cells to attach to a QCM surface and spread over the surface more rapidly, thereby achieving steady state sooner than conventional whole cell QCM biosensors. In addition, the selective whole cell QCM biosensor can be used sooner after cell addition so that more reproducible, sensitive, and accurate results will be obtained from the analysis.

The Selective Whole Cell QCM Biosensor

Figure 1A:
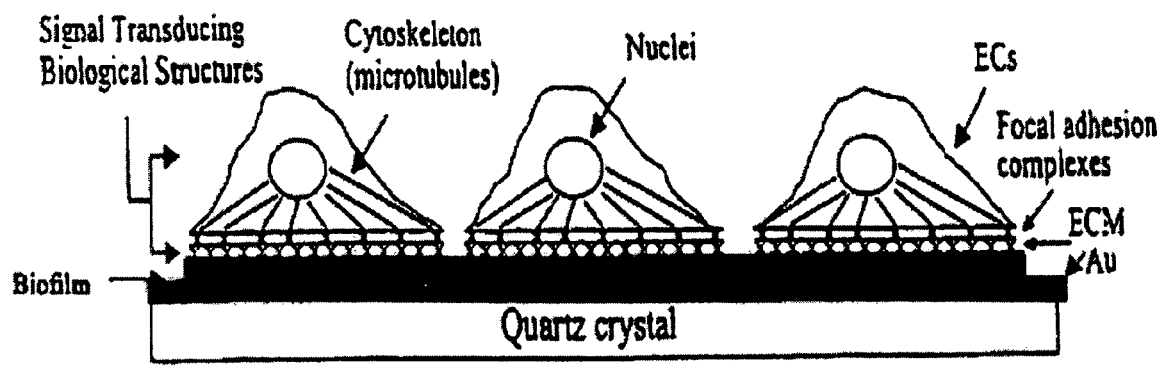
FIGS. 1A to 1D are schematics of a whole cell quartz crystal microbalance (QCM) biosensor.

FIG. 1A illustrates the signal transduction region of a whole cell QCM biosensor, in which a layer or film of a selective substrate is applied to the surface of a conducting element (such as gold (Au)) of the QCM, which is on top of the quartz crystal. This selective whole cell QCM biosensor further contains adherent cells that stably adhere to the selective substrate film or layer and reach a steady state. Initially, the cells adhere to binding sites in the selective substrate film. To reach the steady state, the adherent cells need to synthesize and deposit specific proteins and glycosaminoglycans collectively termed the extracellular matrix (ECM) and spread across the surface of the selective substrate film, and attach themselves more firmly by formation of specific complexes between cell surface molecules and the selective substrate film binding sites, e.g., to form focal adhesion complexes (FACs), to which the cytoskeleton of the cells is coupled. The cytoskeleton allows the cells to stretch and spread, acquiring a greater area on the attachment surface. A principle structural component of the cytoskeleton is an array of microtubules. If the selective substrate film contains ECM molecules or mimetics of these molecules as the binding sites, the cell spreading will be more rapid by eliminating the need for this new synthesis. The QCM and its conducting element, the selective substrate film, and whole, living cells, form the signal transduction elements of the selective whole cell QCM biosensor. These signal transduction elements are then used together with a measurement and/or analysis system in the QCM to form the complete selective whole cell QCM biosensor.

QCMs and Conducting Elements

The QCM technique is based upon the piezoelectric effect, which is a crystal oscillation brought about by an alternating electric field applied across opposite sides of a quartz crystal. In general, a quartz crystal's oscillation frequency shifts if a mass is bound to the crystal surface. The mass required to create a detectable shift is only about 1 ng, illustrating the extreme mass sensitivity of the QCM technique. Appropriate oscillator circuits connected to the surface electrodes can overcome energy losses and stabilize the mechanical oscillation at the resonance frequency. The cut-angle with respect to crystal orientation (i.e., so-called AT cut) determines the mode of oscillation. For example, AT-cut quartz crystals can have a cut angle of 35° 10' with respect to the optical axis. Such crystals perform shear displacements perpendicular to the resonator surface.

The QCM in the QCM biosensor described herein can be a liquid phase QCM system. Such a system consists of an oscillator circuit and a slice of AT-cut piezoelectric quartz crystal. Metal film electrodes are deposited onto both sides of the quartz crystal, one side being a working electrode in an electrochemical cell. The metal electrodes produce an alternating electric field that drives the quartz crystal to oscillate at a characteristic constant frequency, determined by the crystal mass. An increase in any form of bound elastic mass on the quartz crystal surface causes the crystal to change its oscillation frequency according to the Sauerbray equation, which can then be used to quantify, with ng sensitivity, the amount of mass added to the crystal surface. For energy dissipating bound masses on the crystal surface, such as living cells, the change in crystal frequency reflects two attributes: the bound mass magnitude and the viscoelastic properties of the bound mass.

The conducting element of the whole cell QCM biosensor can be made of any suitable conducting material, such as a metal (i.e., ITO), e.g., gold, silver, platinum or palladium, or a conducting polymer, e.g., polypyrrole or polythiophene, or polyaniline (see, e.g., Kaufman et al., Phys. Rev. Left., 1984: 53, 2461-2464, 1984). To facilitate the adhesion of a selective substrate film onto the surface of the conducting element, the surface should be hydrophilic. To make the surface hydrophilic, one can treat the QCM surface as described in, e.g., Facci Modification of Electrode Surfaces with Self-Organized Electroactive Microstructures, In Molecular Design o/Nedrode Surfaces, Techniques in Chemistry Series, Vol. XXII. (ed. Royce W. Murray.) John Wiley and Sons, Inc. 1992, 128-129.

The QCM can be used individually or in an array having multiple QCMs, e.g., 4, 8, or 16 or more QCMs. Each of the QCMs has its own conducting surface, set of conducting wires, and output. Such devices, e.g., as those marketed by Elchema Inc. (Postdam, N.Y.), allow one to analyze multiple samples at the same time. Alternatively, one can use an array of 10s, 100s, or 1000s of minute samples on a single QCM surface.

Selective Substrate Films

The selective substrate films of the whole cell QCM biosensor facilitate the attachment of specific cells onto the QCM. The specific cells can be a large group of different, yet specified cells, a specific type of cell, or a subset of cells that all have the same antigen or binding molecule or receptor or recognition molecule for an antibody on their surface. The specific cells can also be a subset of cells labeled with a particular agent that then selectively binds to the binding sites located on the selective substrate film.

A variety of materials can be employed with the whole cell QCM biosensors. Any material that can be adapted (e.g., polymerized) to provide binding sites that are appropriate for the attachment or association of the desired cells are useful. These materials include, but are not limited to, synthetic polymers (e.g., conducting polymers such as pyrroles or thiophenes, anilines, and their derivatives, and non-conducting polymers, such as phenols and their derivatives), biological polymers (e.g., peptides, nucleotides, and carbohydrates), and composites formed from these materials. Examples of the materials also include monomers or polymers that can be polymerized via electropolymerization or enzymatic polymerization, as described herein.

A whole range of monomers that can be polymerized, e.g., via their aromatic ring structures, are useful in forming the selective substrate film, as long as they include binding sites. For example, monomers of tyrosine and tyrosine derivatives, as well as short peptides containing a terminal tyrosine, can be used to form a selective substrate. The short peptides, covalently incorporated into the selective substrate film, provide recognition sequences, e.g., RGD (arginine-glycine-aspartate) (SEQ ID NO:1), utilized by cells to bind to their underlying extracellular matrix (ECM) proteins including fibronectin. Different recognition peptides presented in different extracellular matrix proteins can be incorporated into the selective substrate, providing binding sites for selected cells.

Other biomolecules can also be immobilized to the selective substrate film to provide the binding sites. For example, an antibody that binds to a specific cell type of interest can be attached to the selective substrate film, thereby retaining those cells of interest on the QCM. Examples of such an antibody include anti-HER antibody, which can detect and bind to malignant breast cancer cells. A binding site or moiety that can bind to a molecule to be tested can also be incorporated into the selective substrate film.

As described in the "studying drug transport across natural vascular permeability barriers" section below, such a binding site or moiety provides another biological signal transduction element for the selective whole cell QCM biosensor.

Examples of such a binding site or moiety include antibodies that can bind to a cell surface protein, a cell surface lipid, or a cell surface carbohydrate (e.g., CD75, a sialylated carbohydrate determinant expressed by 48% of gastric carcinoma cells, but not expressed by normal gastric cells). A binding site or moiety can also be a peptide sequence that can bind to a cell surface recognition molecule. For example, the peptide sequence can be RGD (SEQ ID NO:1), which binds to an integrin receptor, or YIGSR (tyrosine-isoleusine-glycine-serine-arginine) (SEQ ID NO:2), which binds to a laminin receptor. The peptide sequence can be one that can bind to an adhesion molecule (CAM) receptor, a cadherin receptor (e.g., a peptide sequence from catenin or L1 glycoprotein), or a growth factor receptor. See e.g., Okegawa T. et al., J. Urol., 67(4):1836-43,2002. In addition, a binding site or moiety can be a biomimetic or an analog of the above-described binding sites or moieties. The above-mentioned cell surface recognition molecules are bound by binding sites in the form of small molecules or other high affinity molecules such as proteins.

A variety of selective substrate film configurations may also be employed with the whole cell QCM biosensors. Surface geometries of the selective substrate film may be planar, spherical, concave, convex, and textured. The surface geometries of the substrate are planar and may be comprised of any two-dimensional shape. The planar substrates can be continuous or micropatterned upon the underlying gold or conducting material surface using existing micropatterning technology. For example, binding sites can be placed on the surface of the QCM in such a way to produce a micropatterned support that contains a large number of separate coated areas. Micropatterning the surface can provide selective cell adhesion on specific regions of the micropatterned surface and can create a uniform physiologic state within all the immobilized cells. Creation of a uniform physiologic state can improve the signal to noise ratio obtained from the homogeneous cell population used to create the biosensor. Furthermore, this technique allows the creation of biosensors composed of arrays of different cell types that can be precisely arranged on the micropatterned surface to control the physiologic state of individual cells or colonies of cells via intrinsic biological cell-cell communication mechanisms.

After cells are added as described below, the resultant micropatterned, selective whole cell QCM biosensor can be used for parallel processing of a large number of cells or treatments to be applied to the cells. A biosensor in the multiwell format can be used in a similar manner.

Living Cells

Virtually any eukaryotic or procaryotic cells can be used in the whole cell QCM biosensor. Examples of the cells include, but are not limited to, primate, rodent, or human cells and cell lines, as well as mixtures of different cell types. While adherent or anchorage-dependent cells are preferred, anchorage-independent cells can also be used. These anchorage-independent cells can be attached to the selective substrate film by incorporating binding sites that specifically bind to these cells. Any naturally occurring normal or diseased cells, as well as genetically engineered (e.g., containing exogenous nucleic acids) cells may be used. In some embodiments, transformed cell lines or tumor cells are used. Cells of mesodermal, ectodermal, and endodermal origin can be used.

As described herein, sensing by the new QCM biosensors can be related to changes in mass distribution or viscoelastic properties of cells associated with changes in the cell on the biosensor. Sensing can also be carried out via electrical or electrochemical detection of molecules or changes associated with the cells on the biosensor. These changes can be related to metabolic alterations, signal transduction events, and changes in the adhesive properties of the cells.

Measurement Systems

Figure 1B:
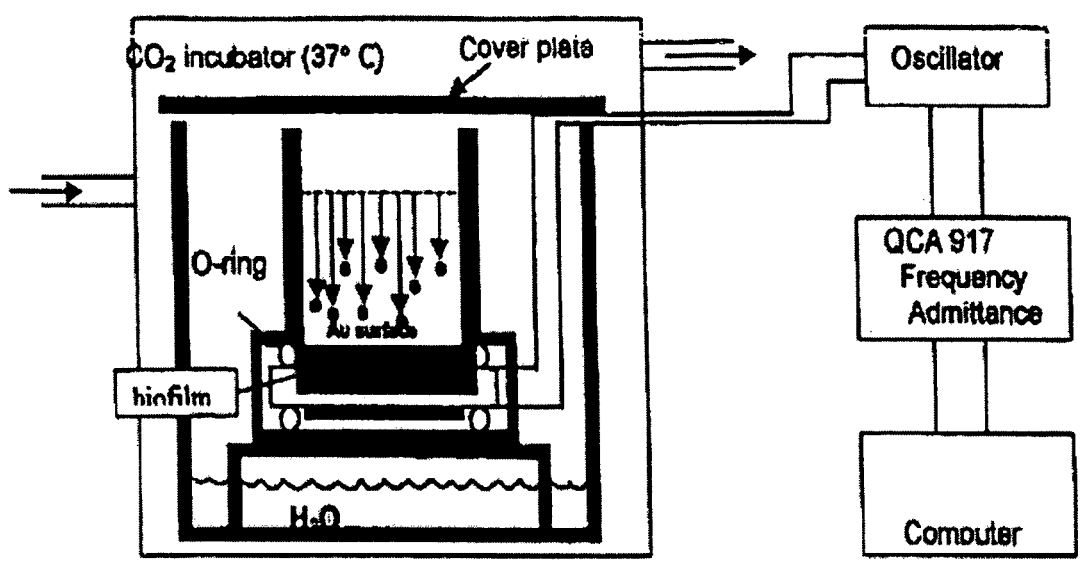

FIG. 1B shows a diagram of a selective whole cell QCM biosensor measurement system. In the system, the whole cell QCM biosensor is sandwiched between two silicone O-rings to allow only one side of its electrode to be exposed to the cell culturing media. The biosensor is placed within a large petri dish filled with distilled water. This water reservoir maintains humidity of the system. The dish is covered with a cover plate and kept inside a 37° C. temperature regulated cell incubator. The QCM can be monitored using any suitable Quartz Crystal Analyzer System.

Figure 1C:
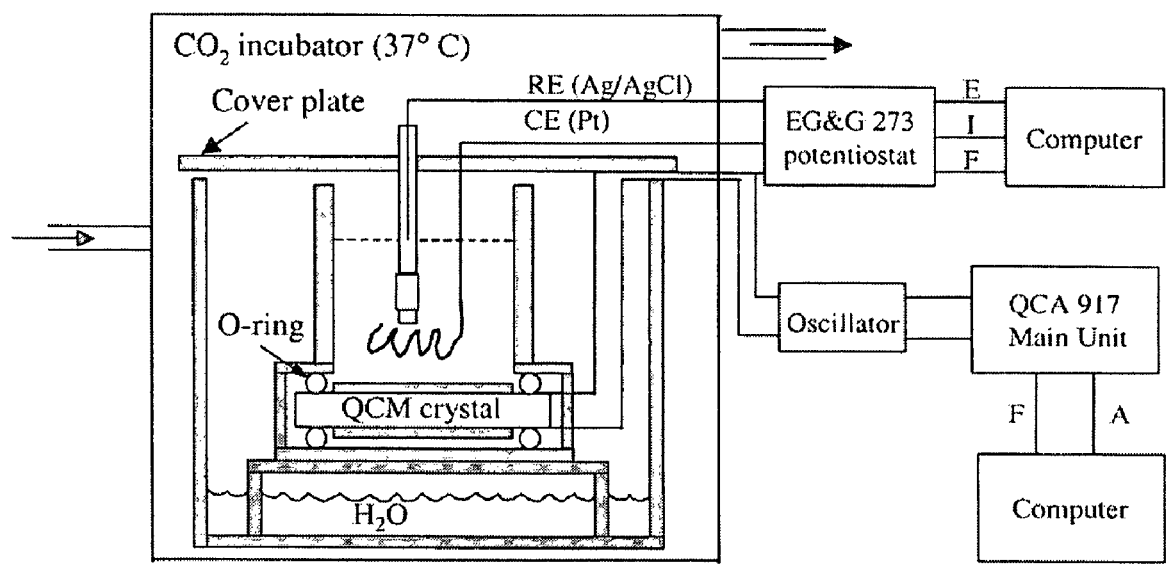

In one example, a Model QCA 917 Quartz Crystal Analyzer System (Seiko EG&G) comprised of a Main Unit and Oscillator is used for the simultaneous measurement of the resonant frequency (f) and resonance admittance (A). In another example (FIG. 1C), a Model EG&G273 potentiostat (Princeton Applied Research, Oak Ridge, Tenn.) is used for measuring the resonant frequency, potential (E), and current (I). In a further example, a VMP2/Z 8-channel Potentiostat Unit (Princeton Applied Research, Oak Ridge, Tenn.) is used to examine potential, current, and impedance (Z) simultaneously. Such a VMP2/Z unit allows one to examine the whole biosensor system via various electrochemistry analyses, e.g., applying constant potential (chronoamperometry), constant current (chronopotentiometry), or sweep potential (cyclic voltammetry). More importantly, it allows one to conduct electrochemical impedance spectroscopy (EIS). All 8 channels of a VMP2/Z unit can be used with one reference electrode and one counter electrode, or they can be used in conjunction with other channels (potentiostats) to perform the same experiment on different electrodes (on different QCM surfaces). In the latter case, each of the channels can be controlled independently.

Figure 1D:
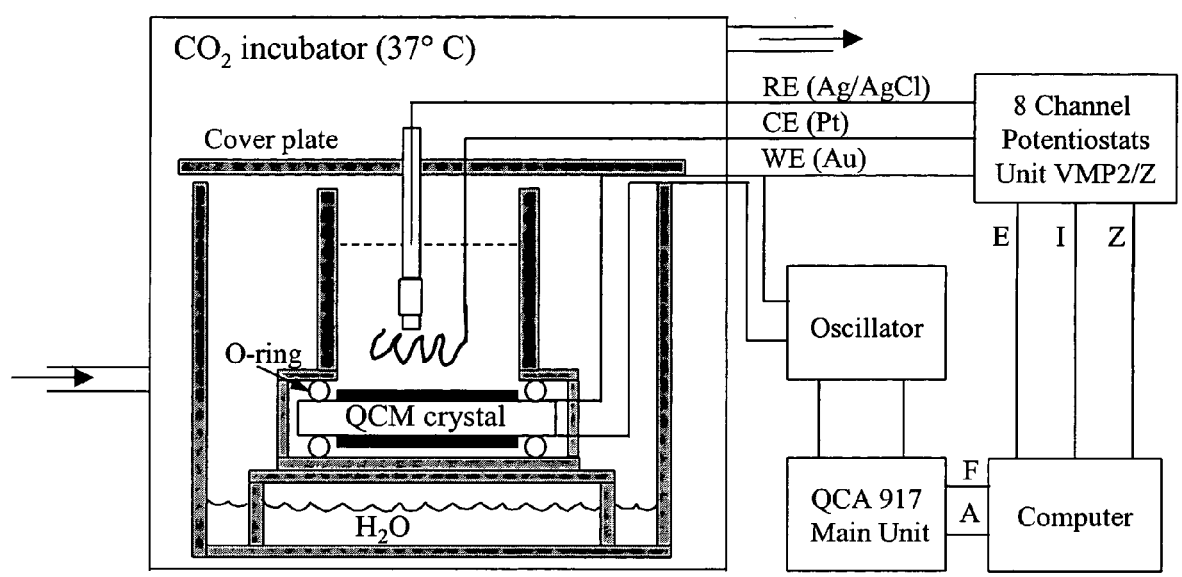

FIG. 1D shows the set-up for one of the 8 channels. Using the VMP2/Z unit, one can gather impedance data and generate impedance plots in the frequency range from 10 Hz to 200 KHz for different cell-QCM biosensor systems. One can then correlate the plots with one or more equivalent circuits using standard techniques and find the circuit models that best fit the plots. For example, for a biosensor having cells and a layer of ECM, one can use the Butterworth-Van Dyke (BVD) circuit (Janshoff et.al., Angew. Chem. Int. Ed. Engl., 39(22):4004-4032, 2000). The parameters of a circuit model can be used to describe a cell-QCM biosensor system (e.g., a normal cell-QCM), be compared with those of other systems (e.g., a cancerous cell-QCM), and used in, e.g., cancer diagnosis and drug screening.

Making the Selective Substrate Film

A variety of methods can be used to make the selective substrate film. In one example, an aqueous solution electropolymerization technique is used to create a thin selective substrate film that covalently incorporates recognition peptides capable of binding to specific cell types. Free radical based electropolymerization is used to polymerize monomers, such as tyrosine, tyrosineamide, tyrosine-containing peptides, and other tyrosine derivatives (e.g., decylester of tyrosine), or mixtures thereof, to form the selective substrate film on the surface of the conducting element of the whole cell QCM biosensor. Alternatively, phenol or aniline based monomers can be used to create the selective substrate films by combining them with tyrosine containing monomers of the type mentioned above. Examples of co-monomer mixtures include: nitro-phenol and RGDY (arginine-glycine-aspartate-tyrosine-peptide) (SEQ ID NO:3), and phenol and RGDY. The recognition peptides include RGDY (SEQ ID NO:3) and YIGSR (SEQ ID NO:2). Monomer mixtures have been investigated in the range from 1:1 to 20:1, although higher ratios, e.g., one 20:1 or 50:1, may also have selective binding activity. Total monomer concentrations in the mM concentration range yield robust selective substrate films, although lower concentrations may also be used to create selective substrate films that form more slowly. Monomers can be used in the mM concentration range, e.g., in a phosphate buffer.

Electropolymerization is performed at a constant potential for a certain length of time, or via a repeated cyclic potential sweeping between two preset values, e.g., from 0.0 V to +1.0 V back down to 0.0 V, for up to almost 30 cycles, or until the initial bare electrode current drops significantly due to selective substrate film formation. This cyclic potential sweeping technique is well known in the art, see, e.g., Marx, K A and Zhou T., J. of Electroanalytical Chemistry 521: 53-60, 2002. Due to successive substrate mass deposition and gold surface property alteration at each cycle, substrate formation can be monitored by QCM recording of frequency and resistance shifts.

As mentioned above, short peptides that specifically bind to, or are particularly bound to, a particular cell subpopulation via binding to a specific cell-surface receptor can be incorporated into the selective substrate film to form binding sites. These peptides can include recognition sequences for normal cells or diseased cells, e.g., a metastatic cancer cell. Thus, whole cell QCM biosensors with these peptides are capable of selectively attracting these cells.

In addition to the above-mentioned electropolymerization, enzymatic polymerization can also be used to make the selective substrate film. Examples of enzymes include horseradish peroxidase, soybean peroxidase, and laccase. See, e.g., Sarma R. et al., Materials Science and Engineering, C4, 189-192, 1996. In addition, chemically initiated free radical polymerization of the same monomers can also be used to form the selective substrate film on a QCM as described in e.g., 2. Ayyagari M. et al., Macromolecules, 28, 5192-5197, 1995.

Seeding Cells

In general, cells to be seeded onto a selective substrate film on a QCM surface are cultured according to standard procedures until the cells reach the mid-log growth phase and are then harvested for seeding onto the selective substrate film. For example, cells can be seeded onto a selective substrate film on a QCM using methods similar to that described in, e.g., Marx et al., Biosens. Bioelectron., 16(9-12):773-82, 2001.

In some embodiments, the cells are harvested using standard procedures, such as the trypsin method. These methods produce a collection of all or most of the cells that were grown in the cell culture. In other embodiments, the cells are harvested or treated using techniques that specific types of cells or cells that have certain characteristics to be seeded onto the selective substrate film. For example, prior to being seeded onto the selective substrate film, the cells can be harvested using a solution containing EGTA or EDTA (both are calcium (Ca) chelators). As a result, cells that adhere to a selective substrate film via a calcium-dependent mechanism are selected and can be seeded onto the selective substrate film.

Alternatively, cells that have already been seeded onto and are attached to the selective substrate film can be treated with an EGTA or EDTA-containing solution. Cells adhering to the selective substrate film via a Ca-dependent mechanism detach from the film (and can be washed away), while cells adhering to the film via a calcium-independent mechanism are kept on the whole cell QCM biosensor. Similarly, trypsin and pronase can be used to harvest cells that are sensitive to one of the enzymes and resistant to the other. Alternatively, lower doses of the enzymes than are conventionally used can be applied and remove only weakly attached cells. Specific peptides such as those mentioned above (SEQ ID NOs:1-3) can be individually applied to cells to harvest them from a stock culture by competing with particular cellular binding sites. Thus, select populations of cells can be derived and used to create the biosensor.

A mitotic shake off method can be used to harvest cells that are synchronized in a particular cell cycle phase (Stobbe C. et al., Int J Radiat Biol 78:1149-57, 2002). Having cells synchronized during the creation of the biosensor can reduce the noise and increase the signal output for at least two population doublings, depending on the cell type, (for example, endothelial cell doubling times are about 21 hours, hence they should be synchronized for approximately 42 hours).

Once harvested, a suitable number of cells are seeded onto a QCM. For example, about 5000 to 25,000 cells/cm$^2$ can be seeded onto a selective whole cell QCM biosensor.

After seeding, the biosensor is monitored until the cells reach steady state. At steady state, the number of cells that are firmly attached to the selective substrate film can be determined using standard techniques, such as the method described in Marx et al., Biosens. Bioelectron., 16(9-12):773-82, 2001.

Uses Of Whole Cell QCM Biosensor

The new selective whole cell QCM biosensors can be used in a wide variety of assays to determine the effects of samples, or unknown analytes or agents or known test compounds in samples, on the specific cells that are bound to the biosensor.

Drug Discovery

The selective whole cell QCM biosensors can be used to determine whether a test compound affects the cytoskeleton, shape, cellular mass distribution, viscoelastic property, attachment, membrane, or extracellular matrix of the cells bound to the selective substrate film. Examples of such a test compound include small organic or inorganic molecules, proteins, peptides, peptidomimetics, polysaccharides, nucleic acids, nucleic acid analogues and derivatives, or peptoids. Compounds are tested by (1) applying the test compound to the cells on a whole cell QCM biosensor; (2) monitoring a change in a parameter of the quartz crystal microbalance (e.g., change of the f ($\Delta$f) and/or R ($\Delta$R)); and (3) comparing a value of the change to a predetermined value (e.g., about $-250$ Hz and 80 $\Omega$ for $\Delta$f and $\Delta$R, respectively, at 8 hours after applying the test compound, or about $-110$ Hz and 40 $\Omega$ at 50 hours after applying the test compound), or observing a change in the parameters over time. A difference between the values and the predetermined values, or a change over time, indicates that the test compound affects the cells, and is thus a candidate compound (candidate therapeutic agent). The candidate agent can be further tested to confirm its therapeutic effect or modified to optimize its effect and limit any side effects, and then formulated as a therapeutic agent.

Therapeutic agents thus identified can be used in a therapeutic protocol to treat diseases or infections via altering the above-mentioned cell properties. In particular, the selective whole cell QCM biosensor is useful to identify cytoskeletal poisons, pro-apoptotic drugs, focal adhesion complex effectors, and cytotoxic drugs.

The test compounds can be isolated from naturally occurring substances or synthesized using any of the numerous approaches in combinatorial library methods known in the art, including: biological libraries; peptoid libraries (libraries of molecules having the functionalities of peptides, but with novel, non-peptide backbones, which are resistant to enzymatic degradation but which nevertheless remain bioactive; see, e.g., Zuckermann et al., J. Med. Chem., 37:2678-85, 1994); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule-libraries of compounds (Lam, Anticancer Drug Des., 12:145, 1997).

The selective whole cell QCM biosensor also allows one to rapidly detect differences in the mechanisms of action of different drugs. For example, the anti-cancer drugs nocodazole and paclitaxel (taxol) target microtubules, a key element of the cellular cytoskeleton, which control cell shape, cell mass distribution, and cell attachment at focal adhesion complexes. However, in their early actions, these two drugs have opposite effects on the microtubule: nocodazole depolymerizes microtubules, while paclitaxel hyperpolymerizes microtubules. Based on the distinct measurement readouts from a selective whole cell QCM biosensor that is contacted with nocodazole or paclitaxel, one can detect the different effects on the cytoskeleton exerted by the two drugs.

Differential Diagnosis for Cancer

The selective whole cell QCM biosensor has great utility in differential diagnosis for cancers by providing methods of evaluating the metastatic potential of a test cell from a subject. The method includes: (1) placing a test cell from a subject, e.g., from a biopsy, onto a first selective whole cell QCM biosensor; (2) placing a control cell onto a second selective whole cell QCM biosensor; (3) monitoring changes of the QCM in the first and second biosensors; and (4) comparing any changes in value. The control cell is a normal cell. A statistically significant difference between the values indicates that the test cell is metastatic. For example, on a per cell basis, normal mammary epithelial cells had a decrease in frequency shift that was at least 2 fold (e.g., 4-6 fold) larger than their malignant counterpart at 4 hours after cells were added to QCMs. At the same time, normal cells had an increase in resistance that is about 2 fold larger than their malignant counterparts. In general, the experiments are normalized to a baseline determined by the addition of serum-containing media prior to the addition of cells. Therefore the absolute frequency or absolute resistance is not only the important consideration. It is the shift value and pattern change in frequency or resistance that is compared between crystals receiving different cells.

The difference between the values can also be evaluated over a period of time (e.g., 12, 18, 24, or 48 hours) rather than at one point in time. It may yield a more accurate and informative view of the clinical attributes of the cells being analyzed.

The test cells of a subject are obtained from a tissue of a mammal, e.g., a human or domestic animal, suspected of having cancer. The tissue can be any body tissue type that comprises cells. Preferably the tissue is obtained from a body tissue suspected of comprising cancerous cells. For example, the tissue can be obtained from a biopsy specimen of a patient. Tissue samples can be analyzed immediately using the QCM biosensor of this invention. Alternatively, the samples can be frozen using standard techniques and thawed and analyzed at a later time.

As shown in the Examples below, the whole cell QCM biosensor can detect characteristics of cell subpopulations that correlate with varying levels of metastatic potential. The diagnostic methods described herein can identify subjects having, or at risk of developing, metastatic cancers. Such information is invaluable to both the pathologist in making an initial diagnosis and the oncologist in prescribing a specific treatment and follow up schedule to judge efficacy of the treatment.

A panel of normal cells or malignant cells of different tissue origins can be placed onto different selective QCM biosensors described herein, and parameters (e.g., $\Delta f$ and $\Delta R$) are recorded at different time points after the cells are placed. The resulting data or patterns can be used to generate a database or library. The data or patterns in the database or library can be used as reference values or patterns for evaluating the metastatic potential or determining the tissue origin of a test cell.

Guiding Cancer Therapies

Most cancers are responsive to initial treatments, but often become resistant to further therapy. It is common that cancers develop resistance to a treatment, e.g., a specific chemotherapeutic agent, with which the cancers are treated. It is also common that some cancers are intrinsically resistant to some chemotherapeutic agents. Thus, physicians need to determine whether a treatment will be effective in treating a cancer before starting a therapy regime, and to monitor whether the cancer develops resistance to a treatment.

A selective whole cell QCM biosensor can be used to evaluate the resistance of a cancer cell to a treatment. To do so, one can seed test cells from a patient onto a whole cell QCM biosensor, apply a treatment to the cells, monitor a change in a parameter of the QCM (e.g., $\Delta f$ and/or $\Delta R$), and compare a value of the change to a predetermined value (e.g., about $-250$ Hz and 80 $\Omega$ for $\Delta f$ and $\Delta R$, respectively, at 8 hours after applying the treatment, or about $-110$ Hz and 40 $\Omega$ at 50 hours after applying the treatment.). The predetermined value can be obtained by the same method, using test cells from the patient prior to the treatment, or using normal or known responsive cancer cells of the same tissue origin from which the test cells are taken. A statistically significant difference between the value from the test cells and the predetermined value is an indication that the cancer is resistant to the treatment.

With the information thus obtained, an oncologist can select the treatment with highest efficacy. If a drug resistance should develop during the course of treatment, the oncologist could test a panel of treatments using the new methods to select those drugs that rescue a therapeutic effect against the cancer cells.

Detecting Infectious Pathogens

Pathogens, such as viruses or bacteria, can perturb cells and their attachment to a selective substrate film. Thus, a selective whole cell QCM biosensor can be used to detect the presence of pathogens or toxins produced by them in a sample. The detection is carried out by contacting the sample with the cells of the whole cell QCM biosensor, monitoring a change of the QCM; and comparing a value of the change to a predetermined value (e.g., about $-100\sim400$ Hz and $50\sim100$ $\Omega$ for $\Delta f$ and $\Delta R$, respectively, at 8 hours after contacting the sample.). The predetermined value is obtained by the same method, using a control sample that is free of any pathogens or toxins. A statistically significant difference between the value and the predetermined value indicates the presence of pathogens or toxins in the sample.

Studying Drug Transport Across Natural Vascular Permeability Barriers

There are two major barriers to overcome when administering drugs, the blood-brain barrier and the gastrointestinal (GI) tract barrier. Both of these barriers can be modeled using the new selective, whole cell QCM biosensors.

To evaluate the ability of a test compound to cross the blood-brain barrier, one first incorporates a binding site or moiety for a test compound into the selective substrate film. One then creates a blood-brain barrier model on a whole cell QCM biosensor by seeding endothelial cells onto the surface of a selective substrate film and treating the endothelial cells with conditioned media derived from brain astroglial cells. Growth factors secreted by the brain astroglial cells trigger the endothelial cells to express brain specific proteins, such as zona occludins (ZO) proteins, including ZO1, ZO2, and ZO3. These proteins establish tight junctions between the cells, thereby forming a barrier that mimics the blood-brain barrier.

After the barriers are formed, one can apply test compounds to the barrier. If the test compound cannot pass through the barrier, the compound cannot reach and bind to its binding site or moiety, thereby causing no changes in the QCM parameters. In contrast, if a test compound can cross the barrier, it will reach and bind to its binding site or moiety on the selective substrate film and cause a shift in $\Delta f$ and/or $\Delta R$. By monitoring the shift, one can determine whether a test compound can cross the mock blood-brain barrier.

The GI tract barrier determines the bioavailability of ingested drugs. To evaluate a test compound's ability to across the GI tract barrier, one can model a GI tract barrier on a whole cell QCM biosensor using colonic epithelium that has been treated with retinoic acid (a molecule that induces gland formation and barrier functions of GI tract). Using a method similar to that for identifying test compounds capable of crossing the brain-blood barrier, one can identify test compounds that can cross the GI tract barrier.

EXAMPLES

The invention is further described in the following examples, which do not limit the scope of the invention described in the claims.

Example 1

Making a Selective Substrate Film on a QCM

Phenol and its derivatives tyrosine and tyrosine amide can be electrochemically polymerized to form very thin self-limited selective substrate films (biomimetic films) on metal electrodes under mild conditions. An artificial matrix with high cell adhesion and growth rates is of great importance for the culture of anchorage-dependent cell types. In general, anchorage-dependent cells adhere and grow well on adhesive proteins such as fibronectin, collagens, and vitronectin. Cell attachment to these adhesive proteins proceeds primarily via the interactions of the integrin class of cell adhesion receptors with adhesive proteins. The adhesion proteins listed above have in common an adhesive site located within the proteins consisting of the tripeptidyl sequence, Arg-Gly-Asp (RGD). The idea of this example is to create selective substrate films on gold electrodes with binding sites that include the peptide sequence RGDY (SEQ ID NO:3) containing both the tyrosine amide (Y) with its electropolymerizable group and the cell recognition sequence RGD.

Materials and Methods:

Monomer of L-tyrosine amide hydrochloride was purchased from Advanced ChemTech, Inc. (Louisville, Ky.). Peptides containing cell recognition sequence Ac-RGD-Y-amide {SEQ ID NO:3) and control sequence Ac-RDG-Y-amide (SEQ ID NO:4) with both N-terminus and C-terminus blocked were prepared using standard techniques. Stock solutions of 2 mM L-tyrosine amide and 1 mM Ac-RGD-Y-amide or Ac-RDG-Y-amide were prepared by dissolving 1.3 mg of L-tyrosine amide hydrochloride and 0.7 mg Ac-RGD-Y-amide or Ac-RDG-Y-amide in 3 ml and 1.4 ml pH 7 PBS (0.05 M), respectively. Then 0.2 mM of both L-tyrosine amide and Ac-RGD-Y-amide or Ac-RDG-Y-amide were made by further dilution of the stock solutions with pH 7 PBS. All the solutions were stored at 4° C. in a refrigerator. Different ratios of 1:0, 1:3, 1:20, 0:1 of 0.2 in M Ac-RGD-Y-amide/L-tyrosine amide were prepared by mixing the two 0.2 mM solutions before the electrochemical polymerizations.

The gold electrodes of ECIS arrays and QCM gold electrodes, as well as the three-electrode configuration, are the same as described in Marx et al., Biosens. Bioelectron., 16(9-12):773-82, 2001. All the solutions were made with sterile water and the PBS was further filtered through 0.22 mm cellulose acetate membrane.

Procedures:

The gold electrode was preconditioned by cycling 3 times between 0.0 to 1.0 V at 20 mV/sec in 350 ml of 0.05 M pH 7 PBS, each 3 cycles to a total of 9 cycles to get a stable baseline. Then the PBS was replaced with 350 ml of monomer solution containing certain ratio of RGDY peptide and L-tyrosine amide. Electrochemical polymerization was then initiated by CV cycling between 0.0 to 1.0 V at 20 mV/sec for 10 times, each 3 cycles to a total of 30 cycles (reduced cycles to 6, 15 for tyrosine amide and 15 to RGDY were also tested). The current normally dropped to a large degree within the initial several cycles and then decreased at a reduced speed, and finally stabilized at the end of the 30 cycles, indicating formation of a stable film on the gold electrode.

When a higher monomer concentration (3 mM) was used, a clear oxidation peak was observed at about 0.8 V vs. Ag/AgCl, then disappeared in the second cycle, showing self-limited property of the insulating or passivating layer. Thus, one should also be able to prepare this kind of selective substrate film by the constant potential method (chronoamperometry) by applying a potential larger than the oxidation peak potential, e.g., 1.0 V, for a certain amount of time, e.g., 1 hour.

After the film was formed, the monomer solution was removed and the modified electrode was rinsed several times with PBS and overlaid with 350 ml PBS and stored in a refrigerator at 4° C. until cell plating.

When selective substrate films were created on the gold QCM electrodes, the thickness or the amount of the film deposited on the gold electrode was monitored using the QCM technique to follow the continuous drop in frequency. Additionally, the stable frequency before and after film formation was monitored during the chronoamperometry tests at 0 V vs. Ag/AgCl for a period of 10 minutes (min) and the frequency difference calculated. Both methods gave a similar frequency magnitude, usually between 100 to 170 Hz.

Example 2

Cell Adhesion

The just-described substrate-containing QCM biosensors were tested for their ability to allow cells to attach to and spread over their surfaces. Normal human endothelial cells were cultured according to the method described in Marx et al., Biosens. Bioelectron., 16(9-12):773-82, 2001. After trypsinizing, the same number of cells was seeded onto three QCM surfaces that had been deposited respectively with different films: RGD-Y-amide/L-tyrosineamide (1:3), RGD-Y-amide/L-tyrosineamide (1:20), and tyrosineamide only.

Twenty-four hours later, each of the QCM surface was washed with PBS and immediately fixed with 100% methanol. Following Coomassie blue staining, the cells on the QCM surface were examined under a light microscope and photographed. It was found that cells on the QCM surface having RGD-Y-amide/L-tyrosineamide (1:3) spread well and reached 90% confluence. In contrast, cells on the QCM surfaces having RGD-Y-amide/L-tyrosineamide (1:20) and tyrosineamide only reached about 30% confluence and less than 10% confluence, respectively. Further, among these cells, some showed an abnormal neuronal morphology instead of that characteristic of normal endothelial cells. These results indicate that cells adhere to and spread over the QCM surface containing RGD-Y-amide (SEQ ID NO:3) in an RGD dose-dependent manner.

Example 3

Cancer Diagnosis Based on Steady State Frequency or Resistance Shift

Normal human mammary epithelial cells (HMEC), estrogen receptor-positive human breast cancer cells (MCF-7, a non-metastatic, malignant mammary epithelial cells), and estrogen receptor-negative metastatic human breast cancer cells (MDA-MB-231) were used for this study. These commercially available cells were cultured and harvested as recommended by the supplier, American Type Cell Cultures (ATCC). The cells were then seeded onto the chemically modified conducting surface of separate whole cell QCM biosensors and were allowed to reach the steady state. In general, it takes about 12-14 hours (hours) or less (as quick as within 6 hours) for the cells to reach the steady state on the new selective whole cell QCM biosensors. In contrast, on a QCM biosensor without the selective substrate, it takes about 20-24 hours for the cells to reach steady state. Cell number-dependent characteristic $\Delta f$ and $\Delta R$ shift values of these cells were recorded as described in Marx et al., Biosens. Bioelectron., 16(9-12):773-82, 2001.

Figure 5:
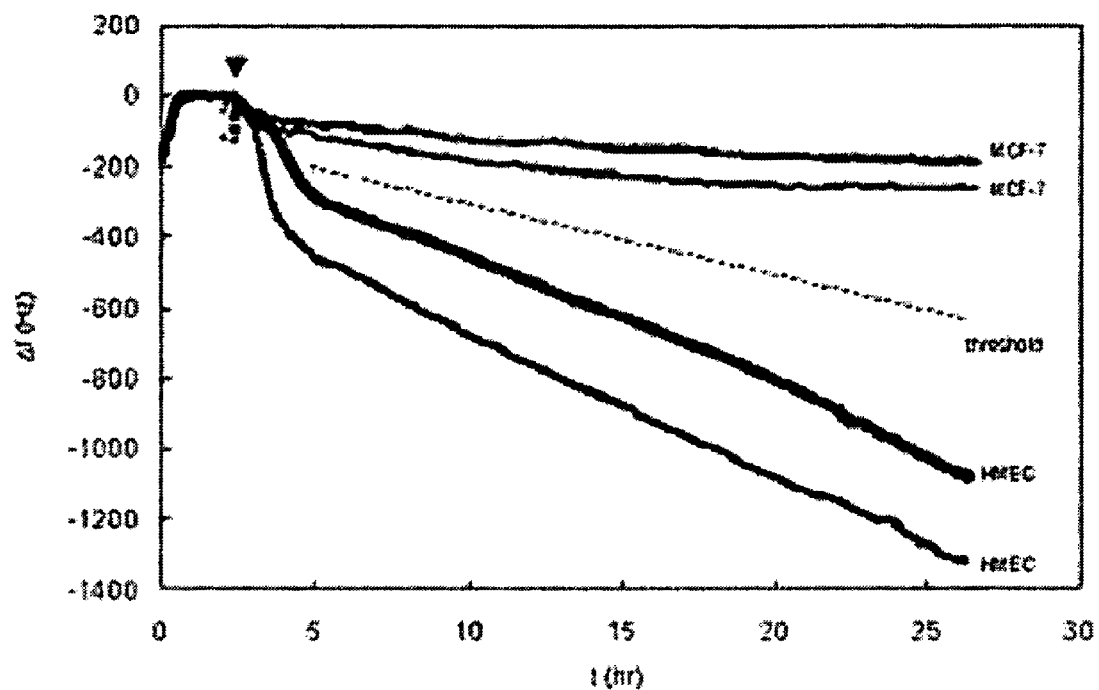
FIG. 5 is a graph illustrating the change in frequency ($\Delta f$) response as a function of time following the addition of cells (at the arrowhead) to form a QCM biosensor with MCF-7 cells and human mammary epithelial cells (HMEC). The dashed line indicates the position of a potential differential diagnostic threshold boundary region that can discriminate between normal and low metastatic breast cancer cell types in a clinical needle biopsy sample. Duplicate experiments were performed using MCF-7 cells and HMEC cells.

As shown in FIG. 5, the $\Delta f$ and $\Delta R$ shift values of MCF-7 (malignant cells) are significantly different from those of normal human mammary epithelial cells (HMEC). On a per cell basis, and at as early as 4 hours following addition of cells to the QCM, normal cells achieved a reproducible 4-6 fold larger decrease in frequency shift compared to their malignant counterpart. Normal mammary epithelial cells also had a nearly two fold higher resistance increase compared to their malignant counterpart. With continuous monitoring over a 20-24 hour period, the differences became more pronounced.

These results indicate that the whole cell QCM biosensor can be used for the detection and diagnosis of cancer cells.

Example 4

Cancer Diagnosis Based on Differences in ECM

The above-described QCM biosensor was used to study cells and the ECM made by the cells. 50,000 normal capillary endothelial cells were seeded onto the QCM and maintained in DMEM-10% Calf Serum for 3-4 days to synthesize ECM.

The cells were then removed by incubating in PBS-0.25 mM EGTA three times for 6 hours according to the method described in Paige et al., Cell Dev. Biol., 27A:151-157, 1991. During this process, the frequency and resistance of the QCM were recorded and plotted.

Figure 2:
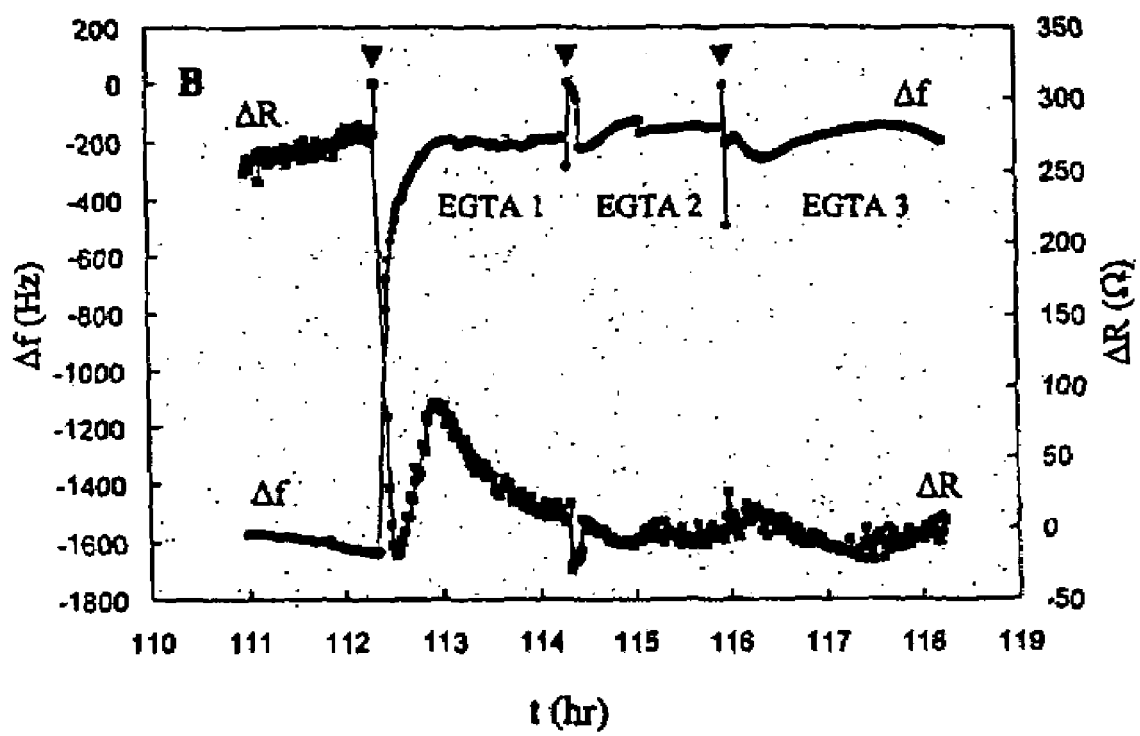
FIG. 2 is a graph illustrating the changes in frequency ($\Delta f$) and resistance ($\Delta R$) as functions of time following the addition of EGTA to cells (at the arrowheads).

As shown in FIG. 2, the initial exposure to PBS-EGTA ("EGTA 1" at hour 112 after cell seeding) immediately resulted in a large decrease in $\Delta R$ and a large increase in $\Delta f$. The frequency and resistance then returned to stable values within 2 hours, suggesting rapid detaching of cells from the QCM surface. The second and third EGTA treatments ("EGTA 2" and "EGTA 3") did not result in significant changes, indicating that the majority of the cells had been removed. To corroborate this discovery, immunocytochemistry was carried out to examine actin stress fiber in the cells using standard techniques. It was found that, at minute 5 after exposing to EGTA, the cells showed actin stress fibers. By minute 120, most cells had detached from the surface.

Figure 3:
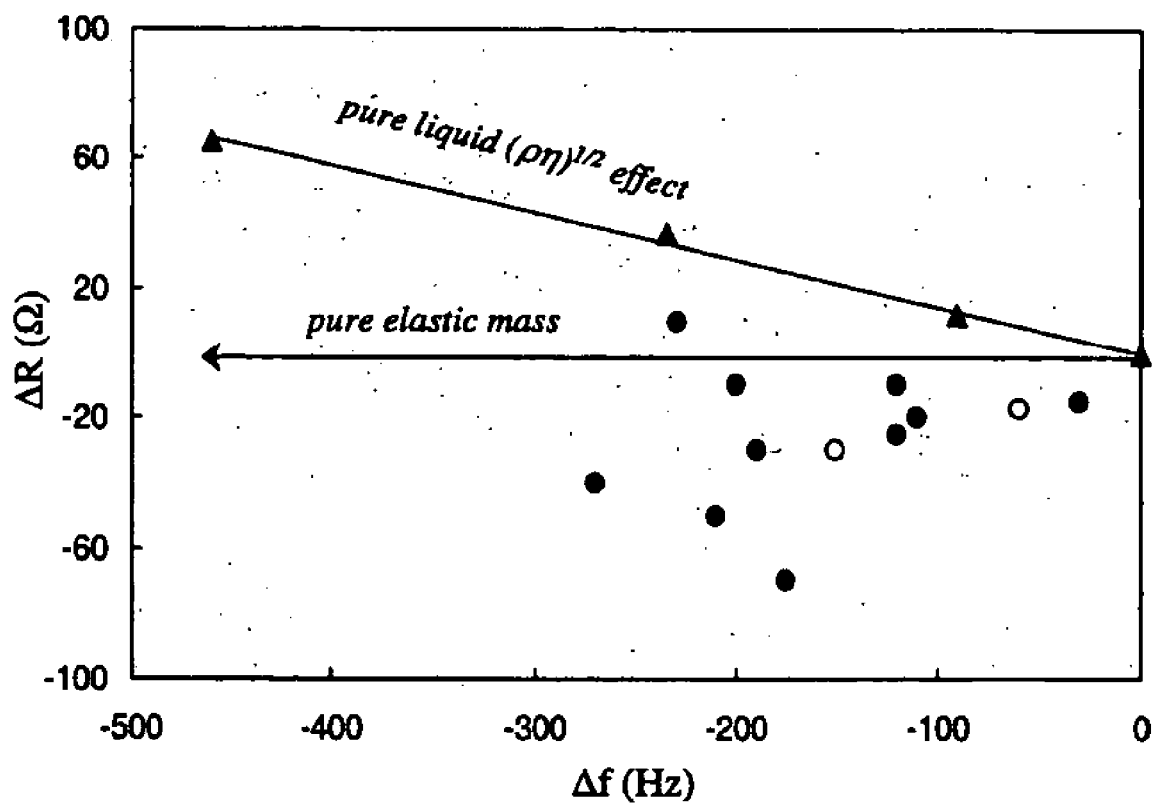
FIG. 3 is a graph showing the change in frequency of a QCM biosensor ($\Delta f$) having an extracellular matrix (ECM) as a function of the change in resistance ($\Delta R$) (Filled circles: ECM produced by normal endothelial cells; Open circles: ECM produced by cancerous MCF-7 cells; Triangles with linear fit: sucrose solutions representing Newtonian fluid behavior to show a pure viscosity-density effect).

The above cell removal experiment was repeated using different numbers of normal endothelial cells and MCF-7 human breast cancer cells. The corresponding steady state $\Delta R$ values and $\Delta f$ values were plotted against each other. As shown in FIG. 3, the plots are close to the zero slope elastic mass behavior line, indicating that no energy was dissipated at the steady state. In addition, the plot of MCF-7 cells differs from that of normal endothelial cells, indicating that the QCM biosensor can be used to detect and diagnosis cancer cells based on this difference.

Example 5

Cancer Diagnosis Based Cell-Cell Cooperativity During Cell Adhesion

Different numbers of normal human endothelial cells were seeded onto a series of QCM biosensors described above. The frequency and resistance of each QCM was monitored during cell attachment to and spreading over the QCM surface according to the method described in Marx et al., Biosens. Bioelec., 16:773-782, 2001; Marx et al., Biotech. Prog., 19:987-999, 2003; and Zhou et al., Biotech. Prog., 16:268-277, 2000. It was found that, at 10 minutes after seeding, more than 50% of the cells contacted the QCM surfaces. However, $\Delta f$ or $\Delta R$ was not recorded until after that time.

Figure 4A:
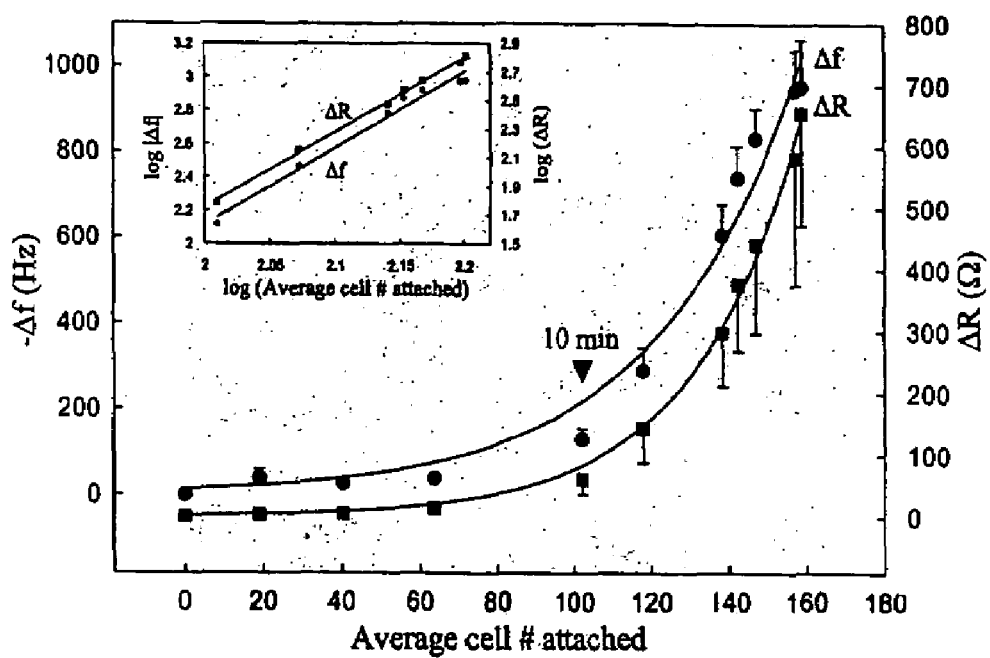
FIGS. 4A and 4B are graphs illustrating the cell-number-dependent behavior of the whole cell QCM biosensor created by the addition of endothelial cells.

A parallel experiment was carried out in the same manner except that the cells were seeded onto the surfaces of 8-chamber Labtek® tissue culture dishes. At different time points, the attached cells were stained with Coomassie blue or immunostained with anti-actin antibodies using standard methods, examined under a microscope, and counted. The cell numbers thus-obtained were used as substitutes for the numbers of cells attached to the QCM surfaces described above at corresponding time points, and plotted against the values of $\Delta f$ and $\Delta R$. As shown in FIG. 4A, each plot fits well with an exponential function. These results suggest cooperativity among the cells.

Figure 4B:
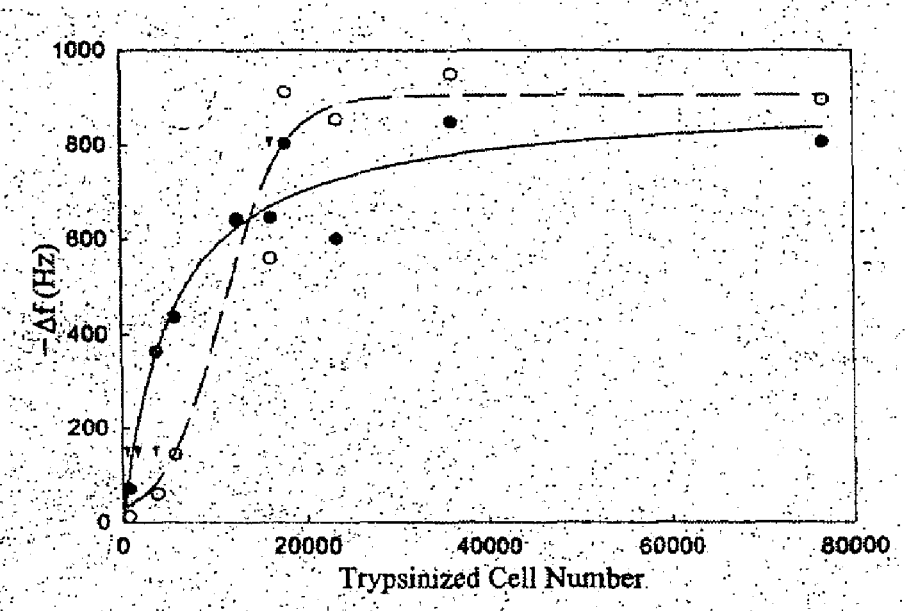

In another experiment, endothelial cells were seeded onto a series of QCM biosensors, and the corresponding frequencies were monitored during cell adhesion for 1 and 24 hours according to the method described above. At the end of the experiment, the cells on each QCM were trypsinized and the cell number was determined using a standard technique. The $\Delta f$ values thus obtained were plotted against the cell numbers. As shown in FIG. 4B, the data obtained at 1 hour produced a sigmoid-shaped curve, indicating cell-cell cooperativity.

It is known that tumor cells proliferate without regard to cell-cell contact. It is expected that tumor cells attach to surfaces in a non-cooperative manner. Accordingly, the above results suggest that the new QCM biosensors can be use to detect the presence or absence of cell-cell cooperativity, and thereby, to diagnose normal vs. cancer cell behavior (when cooperativity is lacking in cancer cells). It is also known that many factors are essential for cell-cell contact and adhesion. Examples of such factors include proteins in tight junctions, adherent junctions, gap junctions, desmosomes, and hemidesmosomes. The new QCM biosensors therefore can be used to examine the functions of these factors and to screen for compounds that regulate the functions.

Example 6

Evaluating Metastatic Potential

MDA-MB-231 cells and HMEC cells were seeded on individual selective whole cell QCM biosensors as described above. The $\Delta f$ and $\Delta R$ shifts were monitored. The $\Delta f$ and $\Delta R$ shifts detected in the HMECs differed significantly from those detected in the MCF-7 cells.

Specifically, as shown in FIG. 5, after being added onto the QCM biosensors, MDA-MB-231 cells quickly (within 8 hours) reached the steady state. The $\Delta f$ dropped to between −170 and −200 Hz. In contrast, the $\Delta f$ of HMEC cells quickly dropped to the range between −350 and −450 Hz range during the first 3-4 hours, followed by a slow decrease to between −1000 and −1300 Hz. Based on the $\Delta f$ shifts, the difference between the HMECs and the MDA-MB-231 could be detected as early as 8 hours after the cells were seeded onto the whole cell QCM biosensors. These data show that the QCM biosensor can be used to rapidly distinguish metastatic, malignant cells from normal cells.

Example 7

Evaluating Metastatic Potential of Cells from Frozen Biopsy Samples

A breast biopsy tissue sample was taken from a patient in the Saints Memorial Medical and Cancer Center and stored in sterile Hanks Balanced Salt Solution (HBSS) containing 5 mg/ml of bovine serum albumin (BSA) on ice. Within one hour, the tissue sample was split in two halves. One half (i.e., a fresh sample) was immediately analyzed. The other half (i.e., a frozen sample) was frozen at −70° C. in a medium containing 15% DMSO, 50% serum, and 35% DMEM.

The fresh sample was then washed with HBSS and homogenized in a Teflon®/glass Potter Elvejhem tissue grinder (0.25 mm clearance) at 400 rpm for 20 times. The homogenized sample was suspended in 10 ml of HBSS containing collagenase and dispase (2 mg/ml each) and incubated on a shaker (150 rpm) at 37° C. for 45 minutes. The resultant homogenate was then centrifuged at 1000 rpm for 10 minutes in a refrigerated tabletop centrifuge to generate a supernatant. Cells in the supernatant were counted using a coulter counter. The supernatants having more than 90% viable cells were further analyzed. More specifically, 20,000 cells were placed on a QCM biosensor, and the frequency and resistance of the QCM were recorded.

Figure 6A:
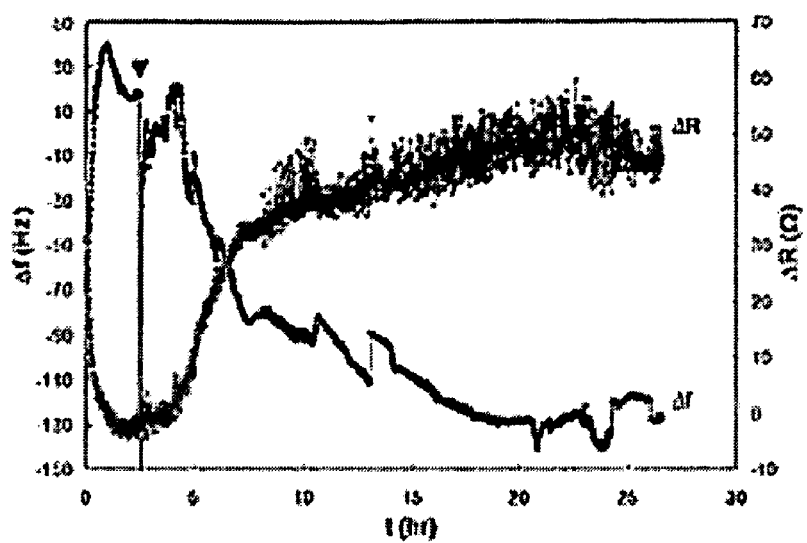
FIGS. 6A and 6B are graphs showing the time-dependent behavior of a whole cell QCM biosensor created by the addition of cells prepared from a fresh tissue (A) or from a frozen and subsequently thawed tissue (B) at the first arrowhead.
Figure 6B:
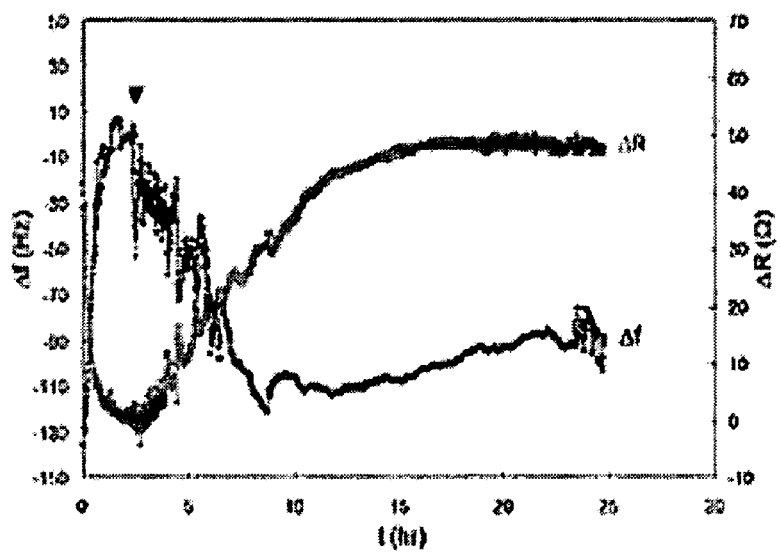

Three months later, the frozen sample was analyzed in the same manner except that, prior to the experiment, it was thawed using standard techniques. The results are summarized in FIGS. 6A and 6B.

As shown in the figures, at 24 hours after cell seeding, the frequencies of the biosensors having cells from the fresh sample and the frozen sample shifted by about −150 Hz and −120 Hz, respectively. According to Examples 3 and 6 described above, both samples were determined to contain malignant cells (i.e., the frequency shifts were above the threshold line shown in FIG. 5). Pathologists later confirmed that the patient, from whom the samples were taken, had a stage IV malignant breast cancer. These results indicate that both fresh and frozen samples can be used in the biosensor of this invention to diagnose cancer.

Example 8

Detecting Drug-Resistance

MCF-7 cells, which are resistant to paclitaxel treatment and MDA-MB-231 cells, which are sensitive to paclitaxel treatment were seeded onto two separate whole cell QCM biosensors and allowed to reach steady state as described above.

Paclitaxel (Sigma Chemical Company) was dissolved in dimethylsulfoxide to make a stock solution. The stock solution was properly diluted in culture media before being added to the cells on the QCM biosensors, so that the final concentration was 10 µM. Paclitaxel is known to maximally inhibit the growth of cells at this concentration. After adding paclitaxel, the Δf and ΔR of the QCMs were monitored and recorded hourly.

Figure 7A:
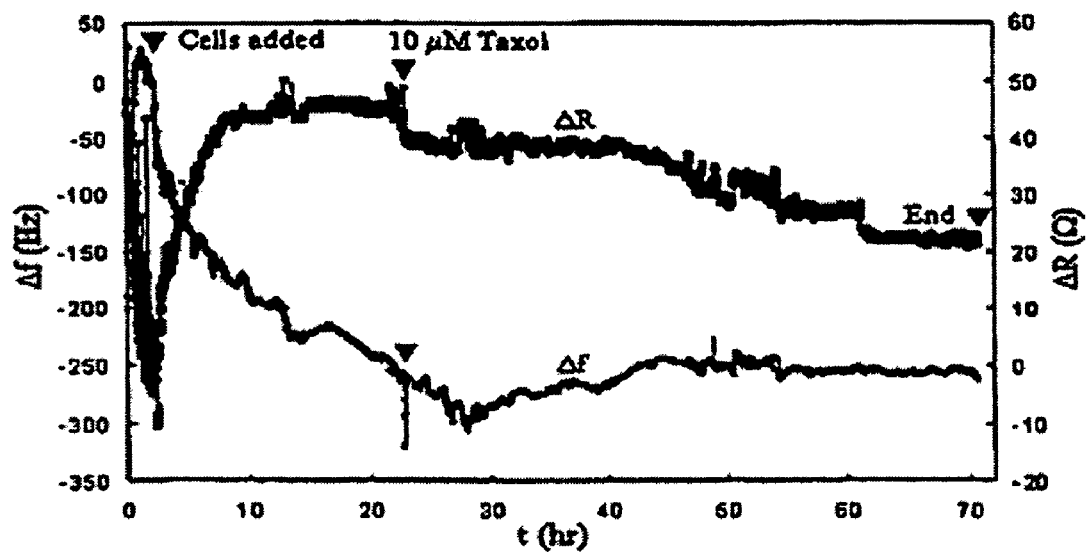
FIGS. 7A and 7B are graphs illustrating the time-dependent behavior of the whole cell QCM biosensor created by the addition of MCF-7 (A) cells or MDA-MB-231 cells (B) at the first arrowhead ("Cell added"). The $\Delta f$ and change in resistance ($\Delta R$) values were recorded continuously until steady state properties were observed. At the second arrowhead, paclitaxel (taxol) was added to a final 10 µM concentration.
Figure 7B:
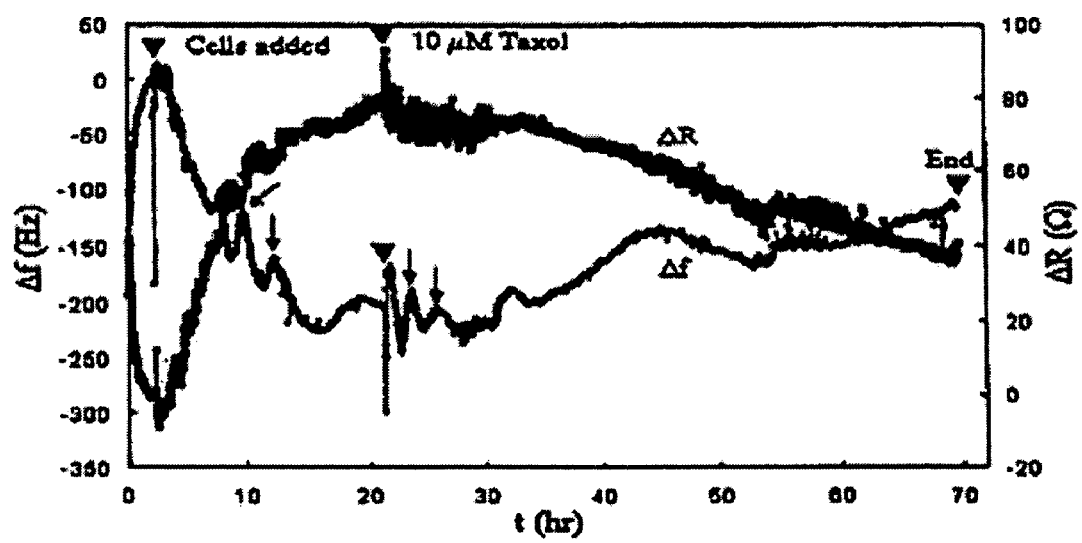

As shown in FIGS. 7A and 7B the MCF-7 cells (FIG. 7A) appeared to behave similarly to the MDA-MB-231 cells (FIG. 7B) in the early response to paclitaxel (1-6 hours post drug treatment), but had a diminished secondary (7-24 hours post drug treatment) response. Immediately after adding the drug, the Δf of both whole cell QCM biosensors decreased. The magnitude of the decline ranged from 60 to 80 Hz. Meanwhile, the ΔR decreased by 50 Ω (MCF-7, FIG. 7A) or increased by about 70 Ω (MDA-MB231, FIG. 7B). During the next 6 to 7 hours, oscillating Δf and ΔR values were observed in both sensors. At 8 hours post paclitaxel addition, rising Δf and decreasing ΔR values were observed. Between 8 and 50 hours post paclitaxel addition, the Δf of MCF-7 steadily increased from −300 Hz to −260 Hz, and the ΔR decreased from about 40 Ω to about 20 Ω. In contrast, the Δf of MDA-MB-231 cells increased from −250 Hz to −110 Hz, and the ΔR decreased from about 80 Ω to about 40 Ω. Note that the magnitude of changes of Δf and ΔR detected in MCF-7 cells (40 Hz and 20 Ω) were much smaller than those detected in MDA-MB-231 cells (140 Hz and 40 Ω respectively).

Duplicate MCF-7 or MDA-MB-231 cells that were treated with the same dose of paclitaxel were analyzed using an apoptosis assay as described in Warren M. et al., Free Radic Biol Med. 29:537-47, 2000. Briefly, cells were fixed sequentially in 50% and 100% methanol for 5 minutes each. The cells were then stained with 4,6,diamidino-2-phenylindole (DAPI; Sigma) at a final concentration of 0.5 mg/ml at 37° C. for 30 minutes. After being air-dried and mounted with 1:3 PBS-glycerol, chromatin distribution in the cells were visualized by fluorescence. Cells were identified as apoptotic if they displayed condensed and fragmented chromatin. Apoptosis was scored as the percentage of apoptotic cells in relation to the total cell number (i.e., Apoptotic Index), corrected for baseline apoptosis. Mitotic cells were also identified and mitosis was scored as the percentage of the mitotic cells in relation to all of the cells (i.e., Mitotic Index). The results showed that, starting at 8 hours post paclitaxel addition, MCF-7 cells and MDA-MB-231 cells began to undergo an obvious cell shape change and eventually apoptosis. See Table 1 below. It was also found that apoptosis of MCF-7 cells was less severe than that of MDA-MB-231 cells. The results indicate that MCF-7 cells are more resistant to the paclitaxel-induced apoptosis.

TABLE 1

Mitotic Index (MI) and Apoptotic Index (AI) (%) of MCF-7 and MDA-MB-231 cells in response to a dose range of paclitaxel as a function of time

| | MCF-7 cells | | | | | | | | MDA-MB-231 cells | | | | | | | |
|---|---|---|---|---|---|---|---|---|---|---|---|---|---|---|---|---|
| Hours | 3 MI | 3 AI | 6 MI | 6 AI | 12 MI | 12 AI | 24 MI | 24 AI | 3 MI | 3 AI | 6 MI | 6 AI | 12 MI | 12 AI | 24 MI | 24 AI |
| Dose | | | | | | | | | | | | | | | | |
| 0 uM | 1.7 | 0 | 2.8 | 0 | 4 | 0 | 6.1 | 0 | 1 | 0 | 4.3 | 0 | 5 | 0 | 7.3 | 0 |
| 0.1 uM | — | — | 1 | 1 | — | — | — | — | — | — | 0 | 1 | — | — | — | — |
| 1.0 uM | — | — | 0 | 4.5 | — | — | — | — | — | — | 0 | 8.5 | — | — | — | — |
| 10 uM | 1 | <1 | 0 | 11 | 0 | 25 | 0 | 33 | 0 | <1 | 0 | 10 | 0 | 40 | 0 | 84 |

Paclitaxel has two mechanisms of action mediated by two separate domains. One domain mediates an early effect on the microtubules (microtubule hyperpolymerization), and the second domain mediates a later action (apoptosis). The two-phase shifts of Δf and ΔR shown in FIGS. 7A and 7B are consistent with this two-phase action of paclitaxel. The early responses of MCF-7 and MDA-MB-231 cells (1-6 hours post drug treatment) detected by the whole cell QCM biosensors correlate with the paclitaxel-mediated microtubule hyperpolymerization. The secondary response of the MCF-7 and MDA-MB-231 cells (7-24 hours post drug treatment) correlates with paclitaxel-induced apoptosis. Further, the values of Δf and ΔR shifts detected in MCF-7 cells were much lower than those in MDA-MB-231 cells. This is consistent with the fact that MCF-7 cells are more resistant to paclitaxel than MDA-MB-231 cells.

As the rising Δf and decreasing ΔR correlated precisely with the onset of the apoptotic response (at 8 hours post paclitaxel addition), as well as the kinetics and quantitative differences in the apoptotic responses of different cells, the whole cell QCM biosensor can be used to detect and quantify apoptosis and cytoskeletal alterations as a function of a specific cell type. Accordingly, the whole cell QCM biosensor can be used to identify cells that are resistant to a drug. Further, the whole cell QCM biosensor allows one to monitor apoptosis in real time without the laborious reactions required in conventional apoptosis assays. Thus, the whole cell QCM biosensor-based detection assays have clear advantages over conventional assays.

Example 9

Drug Evaluation

Taxanes, such as docetaxel and paclitaxel, are used for the treatment of many human cancers. However, patients' responses to the drugs are highly unpredictable. In this Example, the new QCM biosensor described herein was used to evaluate the responses of different cancer cells to docetaxel and paclitaxel.

MCF-7 cells and MDA-MB-231 cells were cultured and seeded onto QCM biosensors according to the method described above. The cells were then incubated with 0.1 μM docetaxel (Aventis Pharmaceuticals) and 10 μM paclitaxel. The changes in frequencies and resistances of the QCMs were monitored for 24 hours. The results are summarized in FIGS. 8A-8D.

Figure 8A:
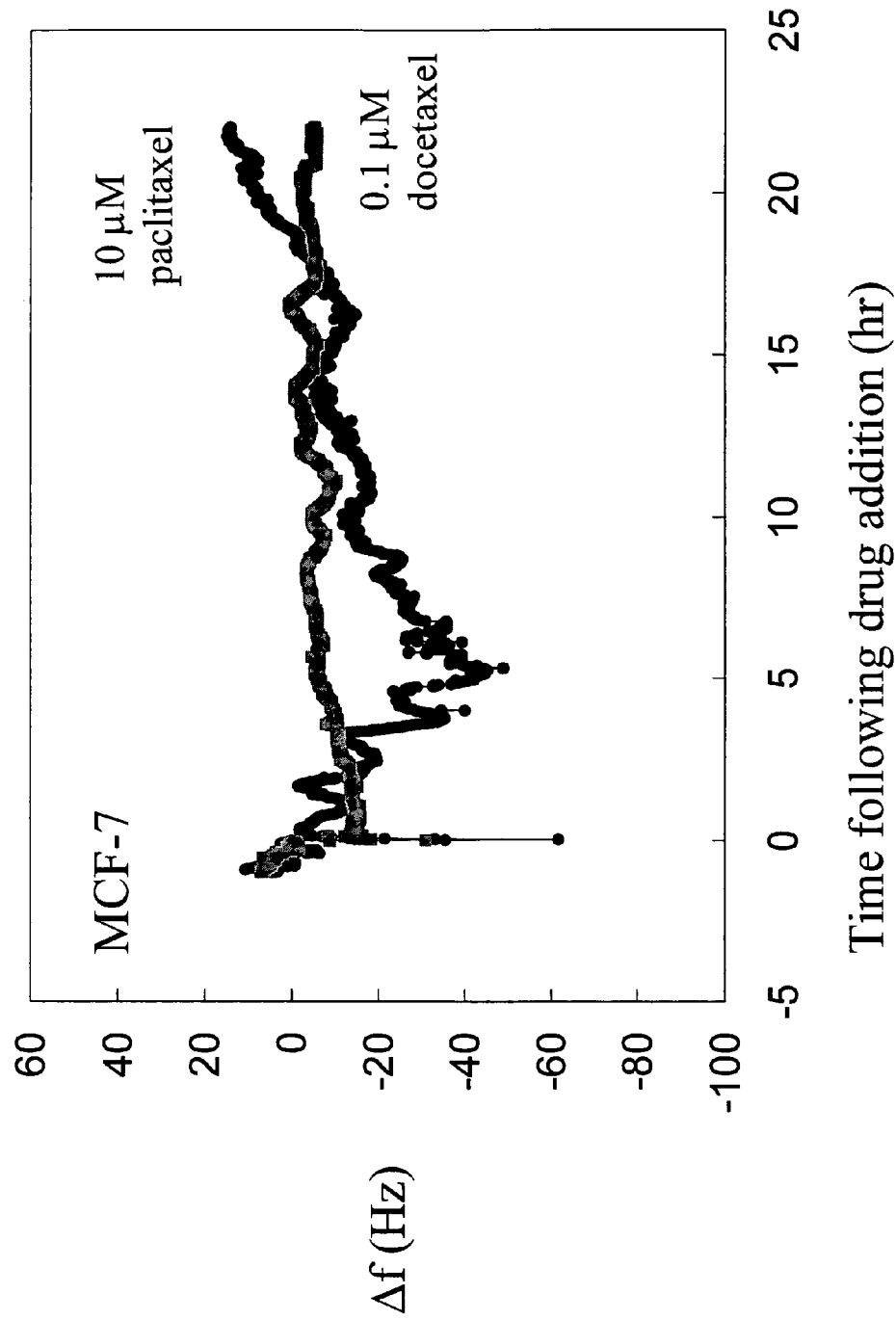
FIGS. 8A-8D are graphs showing the time-dependent behavior of QCM biosensors having MCF-7 cells (A and C) or MDA-MB-231 cells (B and D) that were treated with docetaxel or paclitaxel.
Figure 8B:
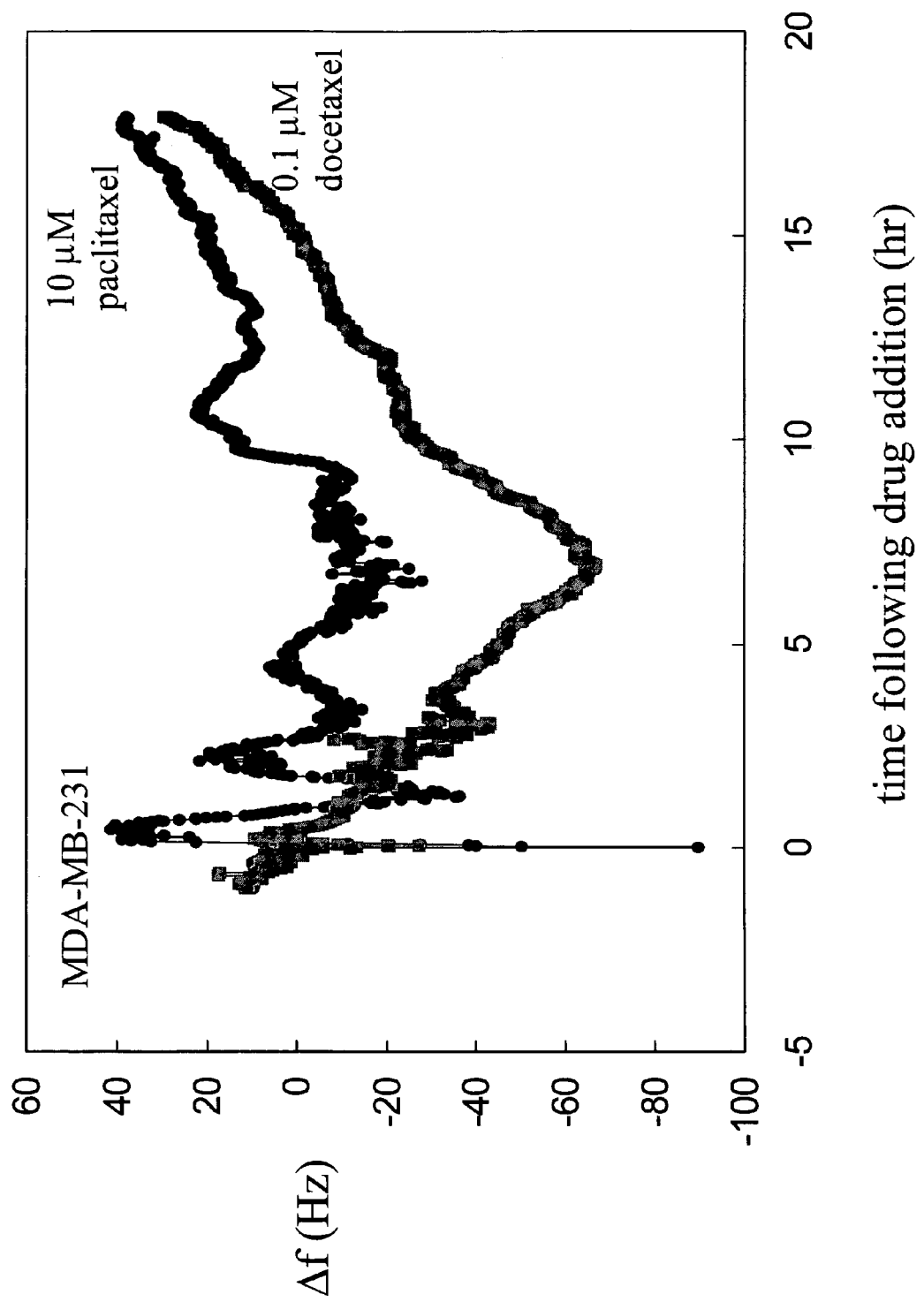
Figure 8C:
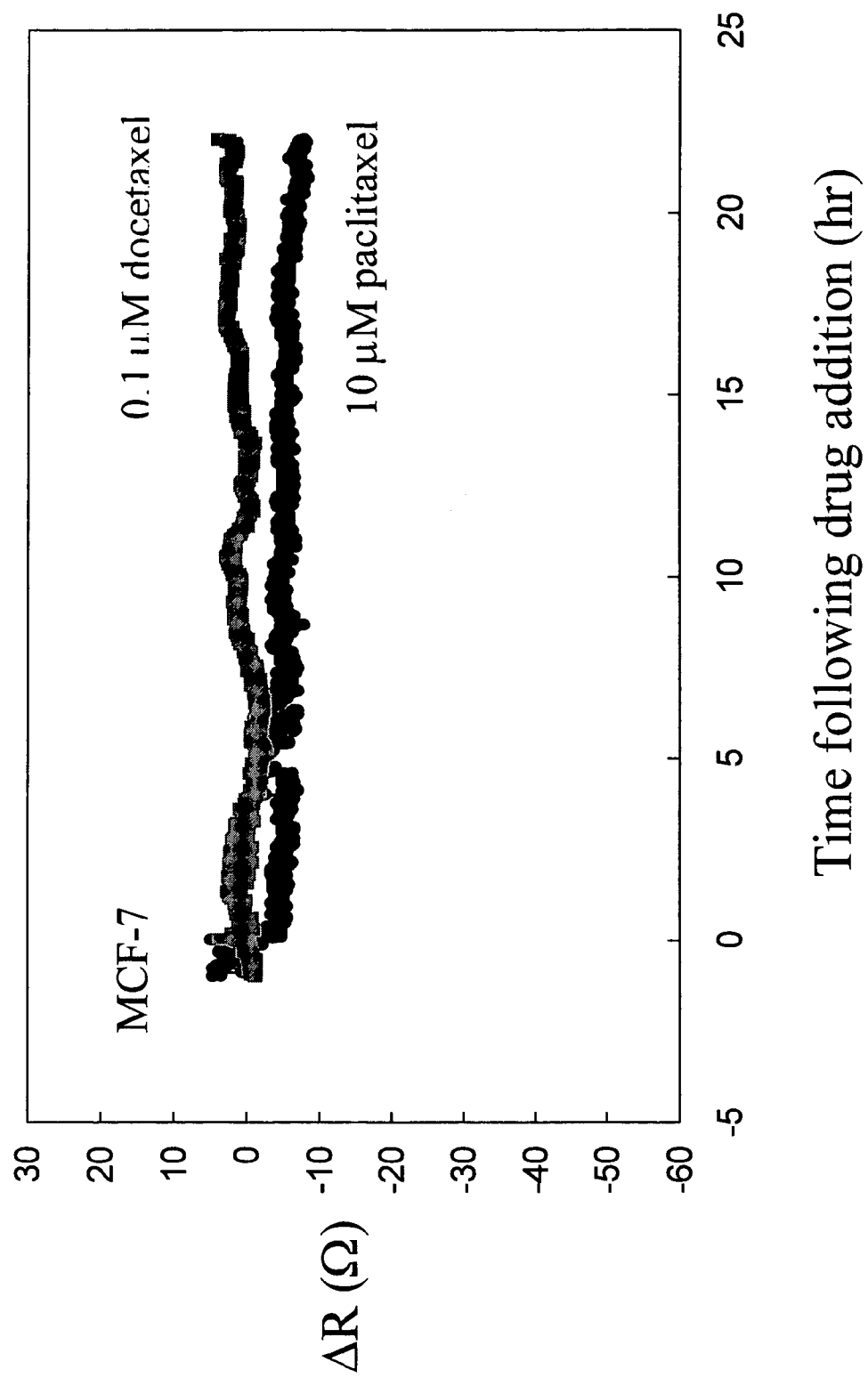
Figure 8D:
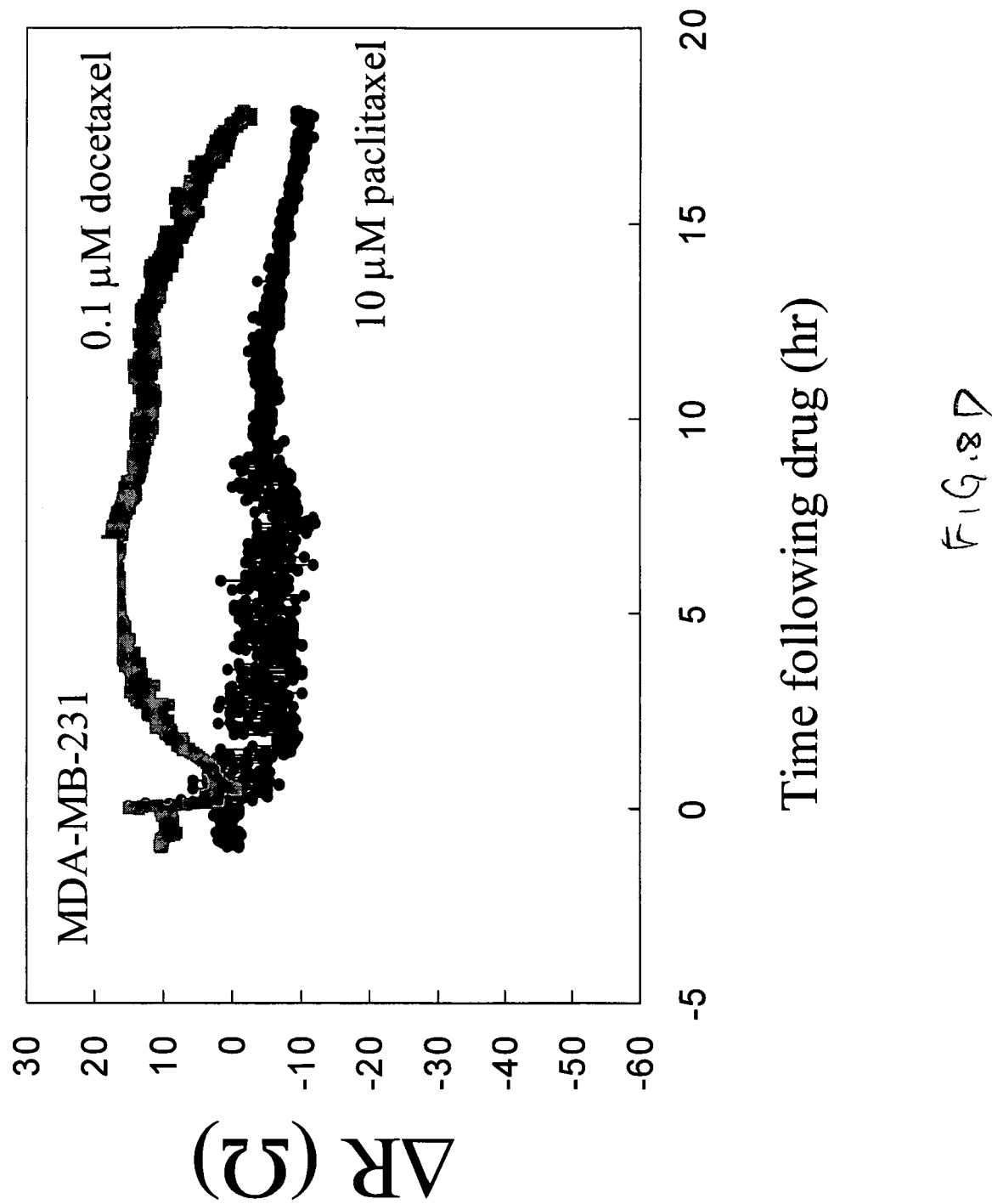

As shown in the figures, from hour 0 to hour 6 post drug addition (Phase I, about t=hours 22-28 on x-axis), the QCM frequencies decreased. In the case of MDA-MB-231 cells (FIG. 8B), the frequency decreased more in response to docetaxel than to paclitaxel (−70 Hz vs. −20 Hz). In the case of MCF-7 cells, the frequency also decreased more in response to docetaxel than to paclitaxel (−50 Hz vs. −20 Hz). Meantime, in response to the drugs, MCF-7 cells caused little change in QCM resistance (FIG. 8C), while MDA-MB-231 cells caused a 20 Ohm increase in response to docetaxel and little change in response to paclitaxel (FIG. 8D).

After hour 6 post drug addition, the frequencies of the QCMs suddenly increased at different speeds. During the period from hour 6 to hour 20 (Phase II, about t=hours 22-28 on x-axis), for MCF-7 cells, the QCM frequency increased by 50 Hz and 10-20 Hz in response to paclitaxel and docetaxel, respectively. In contrast, for MDA-MB-231 cells, the frequency increased by 60 Hz and 98 Hz, respectively.

The above experiments were repeated on MDA-MB-231 cells and MCF-7 cells that were not treated with the drugs. It was found that the corresponding QCM frequencies and resistances remained at the steady state values during Phases I and II.

The above results indicate that MCF-7 and MDA-MB-231 cells respond to the two drugs similarly in Phase I but distinctly in Phase II. During Phase II, MCF-7 cells respond to either drug less than MDA-MD-231 cells.

To confirm that the changes in the QCM frequency and resistance are associated with changes in cell growth or apoptosis, conventional proliferation assays and apoptosis assays were conducted on MDA-MB-231 cells and MCF-7 cells treated with docetaxel or paclitaxel. It was found that both drugs inhibited cell growth and induced apoptosis. For example, both drugs reduced the mitotic index of MCF-7 cells and eliminated that of MDA-MB-231. Also, in response to the drugs, both types of cells showed increased apoptosis. Interestingly, more MDA-MB-231 cells underwent apoptosis than MCF-7 cells, particularly in Phase 11. These results are consistent with the just-described QCM studies, indicating that the changes in the frequency and resistance in Phase II are positively associated with the abilities of the drugs to inhibit cell growth and promote apoptosis.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A biosensor comprising:
a quartz crystal microbalance comprising a conducting element; and
a selective substrate film disposed onto a surface of the conducting element, wherein the selective substrate film comprises one or more binding sites that comprise peptides that are covalently bound to the selective substrate film, and wherein the peptides comprise the amino acid sequence RGDY (SEQ ID NO:3) or YIGSR (SEQ ID NO:2) or both.

2. The biosensor of claim 1, wherein the binding sites comprise the amino acid sequence of RGDY (SEQ ID NO:3).

3. The biosensor of claim 1, further comprising a specific type of cell attached to the selective substrate film by means of a cell-surface molecule bound to a binding site on the selective substrate film.

4. The biosensor of claim 3, wherein the cell is a eukaryotic cell.

5. The biosensor of claim 3, wherein the cell is a mutant cell.

6. The biosensor of claim 3, wherein the cell is a diseased cell.

7. The biosensor of claim 3, wherein the cell is a tumor cell.

8. The biosensor of claim 3, wherein the cell is a breast cancer cell.

9. The biosensor of claim 3, wherein the cell is an endothelial cell.

10. The biosensor of claim 3, wherein the cell is an epithelial cell.

11. The biosensor of claim 1, wherein the selective substrate film comprises a synthetic polymer.

12. The biosensor of claim 1, wherein the binding sites are partially embedded in the selective substrate film.

13. The biosensor of claim 1, wherein the selective substrate film is synthesized by polymerizing a plurality of monomers on the surface.

14. The biosensor of claim 13, wherein the monomers contain phenolic compounds, aniline derivatives, tyrosines, tyrosine derivatives, or a tyrosine-containing peptide, or a combination thereof.

15. The biosensor of claim 13, wherein the monomers are polymerized by electropolymerization.

16. The biosensor of claim 15, wherein the electropolymerization is conducted at a constant potential or at a cyclic potential.

17. The biosensor of claim 13, wherein the monomers are polymerized by enzymatic polymerization.

18. The biosensor of claim 17, wherein the enzymatic polymerization is conducted using peroxidase or laccase.

19. A method of screening an agent for its ability to affect a cell using a biosensor of claim 1, the method comprising
placing a cell onto the biosensor;
contacting the agent to the cell;
monitoring a parameter of the quartz crystal microbalance; and
comparing the parameter with a predetermined value, wherein a difference between the parameter and the predetermined value indicates that the agent has affected the cell.

20. The method of claim 19, wherein the parameter of the quartz crystal microbalance is resonant frequency, resistance, impedance, potential, current, or admittance.

21. The method of claim 19, wherein the cell is a diseased cell.

22. The method of claim 21, wherein the cell is a tumor cell.

23. The method of claim 22, wherein the cell is a breast cancer cell.

24. A method of evaluating the metastatic potential of a test cell from a subject using a first and a second biosensor, each biosensor comprising a biosensor of claim 1, the method comprising:
placing a test cell onto the first biosensor;
placing a control cell onto the second biosensor;
monitoring a parameter of the quartz crystal microbalance (QCM) in the first biosensor and the same parameter of the QCM in the second biosensor; and
comparing the parameters, wherein a difference between the parameters indicates the metastatic potential of the test cell.

25. The method of claim 24, further comprising applying a treatment to the test and control cells prior to the monitoring step.

26. The method of claim 24, wherein the control cell is a wild type cell.

27. The method of claim 24, wherein the test cell is a mutant cell.

28. The method of claim 24, wherein the parameter of the quartz crystal microbalance is resonant frequency, resistance, impedance, potential, current, or admittance.

29. A method of evaluating a metastatic potential of a test cell from a subject using a first and a second biosensor, each biosensor comprising a biosensor of claim 1, the method comprising:
placing a test cell onto the first biosensor;
placing a control cell onto the second biosensor;
monitoring a pattern of a parameter of the quartz crystal microbalance (QCM) in the first biosensor and the pattern of the same parameter of the QCM in the second biosensor; and
comparing the patterns, wherein a similarity in the patterns indicates that the test cell is normal and a difference in the patterns indicates that the test cell is malignant.

30. The method of claim 29, further comprising applying a treatment to the test and control cells prior to the monitoring step.

31. The method of claim 29, further comprising comparing the pattern of the parameter of the QCM in the first biosensor with a third pattern, wherein a difference in the patterns indicates that the test cell is normal and a similarity in the patterns indicates that the test cell is malignant.

32. The method of claim 31, wherein the third pattern is a pattern exhibited by a cancer cell.

33. The method of claim 32, wherein the cancer cell is a breast cancer cell.

34. The method of claim 29, wherein the parameter of the quartz crystal microbalance is resonant frequency, resistance, impedance, potential, current, or admittance.

35. A method for evaluating a treatment for a subject using a first and a second biosensor, each biosensor comprising a biosensor of claim 1, the method comprising
obtaining a test cell from the subject;
placing the test cell onto the first biosensor;
placing a control cell onto the second biosensor, wherein the control cell is not responsive to the treatment;
applying the treatment to the test and control cells; monitoring a parameter of the quartz crystal microbalance (QCM) in the first biosensor and the same parameter of the QCM in the second biosensor; and
comparing the parameters, wherein a difference between the parameters indicates that the treatment is effective.

36. The method of claim 35, wherein the parameter of the quartz crystal microbalance is resonant frequency, resistance, impedance, potential, current, or admittance.

37. The method of claim 35, wherein the treatment is applied by contacting a compound with the test and control cells.

38. A method for evaluating multiple treatments for a subject using a plurality of biosensors, each of the biosensors comprising a biosensor of claim 1, the method comprising:
obtaining a plurality of test cells from the subject;
placing the test cells onto a first array containing the plurality of biosensors;
placing a plurality of control cells onto a second array containing the plurality of biosensors, wherein the control cells are not responsive to the treatments;
applying each of the multiple treatments to the test cells to different locations on the first array and to the control cells at corresponding locations on the second arrays, respectively;
monitoring a parameter of quartz crystal microbalance (QCM) of a biosensor at the location in the first array and the same parameter of the QCM of a biosensor at the corresponding location in the second array; and
comparing the parameters, wherein a difference between the parameters indicates that the treatment is effective.

39. The method of claim 38, wherein the parameter of the quartz crystal microbalance is resonant frequency, resistance, impedance, potential, current, or admittance.

40. The method of claim 38, wherein the treatment is applied by contacting a compound with the test and control cells.

41. A method of detecting an infectious pathogen using a first and a second biosensor, each biosensor comprising a biosensor of claim 1, the method comprising
placing a plurality of test cells onto the first and the second biosensor;
contacting a test sample to the cells on the first biosensor;
contacting a pathogen-free sample to the cells on the second biosensor;
monitoring a parameter of the quartz crystal microbalance (QCM) in the first biosensor and the same parameter of the QCM in the second biosensor; and
comparing the parameters, wherein a difference between the parameters indicates the presence of a pathogen in the test sample.

42. The method of claim 41, wherein the parameter of the quartz crystal microbalance is resonant frequency, resistance, impedance, potential, current, or admittance.

43. The method of claim 41, wherein the pathogen is a virus, a bacterium, a fungus, or a protozoa.

44. A method of screening an agent for its ability to cross a biological barrier using a first and a second biosensor, each biosensor comprising a biosensor of claim 1, the method comprising
adding a plurality of binding site or moiety specific for the agent onto the first and the second biosensors;
placing a plurality of test cells onto the first biosensor; growing the test cells under conditions suitable for forming a biological barrier;
placing a plurality of control cells onto the second biosensor;
growing the control cells under conditions not suitable for forming the biological barrier;
contacting the agent with the test and the control cells;
monitoring a parameter of the quartz crystal microbalance (QCM) in the first biosensor and the same parameter of the QCM in the second biosensor; and
comparing the parameters, wherein a similarity between the parameters indicates that the agent can cross the biological baffler.

45. The method of claim 44, wherein the parameter of the quartz crystal microbalance is resonant frequency, resistance, impedance, potential, current, or admittance.

46. The method of claim 44, wherein the biological barrier is the blood-brain barrier and the test cells contain endothelial cells.

47. The method of claim 44, wherein the biological baffler is the gastrointestinal tract barrier and the test cells contain epithelial cells.

48. A method of making a biosensor of claim 1, the method comprising:
obtaining a quartz crystal microbalance, and
synthesizing a selective substrate film onto the surface of a conducting element of the quartz crystal microbalance, wherein the substrate film contains one or more binding sites that are covalently bound to the selective substrate film, and wherein the binding sites comprise peptides including the amino acid sequence RGDY (SEQ ID NO:3) or YIGSR (SEQ ID NO:2), or both.

49. The method of claim 48, further comprising placing a cell onto the selective substrate film.

50. The method of claim 48, wherein the selective substrate film is synthesized by polymerizing a plurality of monomers on the surface.

51. The method of claim 50, wherein the monomers contains phenolic compounds, aniline derivatives, tyrosines, tyrosine derivatives, or a tyrosine-containing peptide.

52. The method of claim 50, wherein the monomers are polymerized by electropolymerization.

53. The method of claim 52, wherein the electropolymerization is conducted at a constant potential or at a cyclic potential.

54. The method of claim 50, wherein the monomers are polymerized by enzymatic polymerization.

55. The method of claim 54, wherein the enzymatic polymerization is conducted using peroxidase or laccase.

* * * * *

UNITED STATES PATENT AND TRADEMARK OFFICE
CERTIFICATE OF CORRECTION

PATENT NO. : 7,566,531 B2
APPLICATION NO. : 10/793386
DATED : July 28, 2009
INVENTOR(S) : Kenneth A. Marx et al.

It is certified that error appears in the above-identified patent and that said Letters Patent is hereby corrected as shown below:

Column 24

Lines 32-33, in Claim 44, below "comprising" delete "adding a plurality of binding site or moiety specific for the agent onto the first and the second biosensors;"

Line 48, in Claim 44, delete "baffler." and insert --barrier.--

Line 55, in Claim 47, delete "baffler" and insert --barrier--

Signed and Sealed this

Tenth Day of November, 2009

David J. Kappos
*Director of the United States Patent and Trademark Office*